United States Patent [19]
Thøgersen et al.

[11] Patent Number: 5,998,375
[45] Date of Patent: Dec. 7, 1999

[54] NOCICEPTIN ANALOGUES

[75] Inventors: Henning Thøgersen, DK-3520 Farum; Kjeld Madsen, DK-3500 Værløse; Uffe Bang Olsen, DK-2625 Vallensbæk; Nils Langeland Johansen, DK-2100 Copenhagen Ø; Mark Scheideler, DK-2200 København N, all of Denmark

[73] Assignee: Novo Nordisk A/S, Bagsvaerd, Denmark

[21] Appl. No.: 09/115,209

[22] Filed: Jul. 14, 1998

Related U.S. Application Data

[60] Provisional application No. 60/052,862, Jul. 17, 1997.

[30]    Foreign Application Priority Data

Jul. 15, 1997 [DK] Denmark .................................. 0867/97

[51] Int. Cl.$^6$ .......................... A61K 38/00; A61K 38/02; C07K 5/00; C07K 7/00
[52] U.S. Cl. ............................. 514/13; 530/326; 530/300
[58] Field of Search ............................. 514/13; 530/300, 530/326

[56]    References Cited

PUBLICATIONS

J. Rudinger "Peptide Hormones" J.A. Parsons, ed., University Park Press, Baltimore: 1976, Chapter 1.
Ling, et al., "Morphinomimetic Activity of Synthetic Fragments of beta lipotropin and Analogs" Proc. Natl. Acad.
Grant "Synthetic Peptides: A User's Guide" W.H. Freeman & Company, New York: 1992, p. 45.
Dooley et al., *Life Sciences,* vol. 59, No. 1, pp. PL23–29, 1996.
Reinscheid et al., *J. of Biol. Chem,* vol. 271, No. 24, Jun. 14, 1996, pp. 14163–14168.

*Primary Examiner*—Avis M. Davenport
*Attorney, Agent, or Firm*—Steve T. Zelson, Esq.; Reza Green, Esq.

[57]    ABSTRACT

The present invention relates to novel peptides, pharmaceutical compositions containing them, methods for preparing the compounds, use of the compounds for preparing medicaments for treating vasomotor disturbances, in particular the peripheral vasomotor effects known as hot flushes or hot flashes, and to a method of treating vasomotor disturbances.

72 Claims, No Drawings

NOCICEPTIN ANALOGUES

CROSS-REFERENCE TO RELATED APPLICATIONS

This applications claims priority under 35 U.S.C 119 of U.S. Provisional application Ser. No. 60/052,862 filed Jul. 17, 1997, and Danish application 0867/97 filed Jul. 15, 1997, the contents of which are fully incorporated herein by reference.

FIELD OF INVENTION

The present invention relates to novel peptides, pharmaceutical compositions containing them, methods for preparing the compounds, use of the compounds for preparing medicaments for treating vasomotor disturbances, in particular the peripheral vasomotor effects known as hot flushes or hot flashes, and to a method of treating vasomotor disturbances.

BACKGROUND OF THE INVENTION

A "hot flush" is a sudden transient sensation ranging from warmth to intense heat and typically accompanied by flushing and perspiration. It is the classic sign of the menopause and the predominant complaint of menopausal women. Epidemiological studies report that the majority of menopausal women experience hot flushes, although with large variation in frequency and intensity (Treatment of the Postmenopausal Woman, Basic and Clinical Aspects, Raven Press 1994, ed. R. A. Lobo).

A positive correlation between plasma levels of calcitonin gene-related peptide (CGRP) and frequency of hot flushes in women has recently been reported (Chen et al., 1993, Lancet (342) 49), in accordance with the potent vasodilatory effect of CGRP (Brain et al., 1985, Nature, (313) 54–56).

Recently, a novel heptadeca peptide, nociceptin, was discovered (Meunier et al., 1995, Nature (377) 532–535, Reinscheid et al., 1995, Science (270) 792–794).

Nociceptin and analogues thereof have been disclosed in WO 97/07212 and in WO 97/07208. These peptides and inhibitors thereof are said to be useful for antagonising physiologic effects of an opioid in an animal, and for treating/preventing a disease related to: hyperalgesia, neuroendocrine secretion, stress, locomotor activity, anxiety, instinctive behaviour, decreasing of learning, memory, curiosity, attention and/or sensory perception.

SUMMARY OF THE INVENTION

The present invention relates to compounds of the general formula I

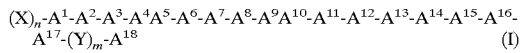

wherein
$A^1, A^2, A^3, A^4, A^5, A^6, A^7, A^8, A^9, A^{10}, A^{11}, A^{12}, A^{13}, A^{14}, A^{15}, A^{16}, A^{17}, A^{18}$, X, Y, n and m are as defined in the detailed part of the present description, provided that there is at least two simultaneous amino acid modifications relative to the nociceptin sequence or an unnatural amino acid in position $A^1$.

The present compounds are particularly useful for the treatment of vasomotor disturbances, in particular the peripheral vasomotor effects known as hot flushes or hot flashes.

Moreover, the compounds of formula I are useful for antagonising physiologic effects of an opioid in an animal, and for treating a disease related to: hyperalgesia, neuroendocrine secretion, stress, locomotor activity, anxiety, instinctive behaviour, decreasing of learning, memory, curiosity, attention and/or sensory perception.

It is an object of the present invention to provide novel compounds being effective against vasomotor disturbances, such as hot flushes or hot flashes.

It is a further object of the invention to provide pharmaceutical compositions, comprising the novel compounds of the invention, being effective against vasomotor disturbances, such as hot flushes or hot flashes.

Further objects will become apparent from the following description.

DETAILED DESCRIPTION OF THE INVENTION

Accordingly, the present invention relates to compounds of the general formula I

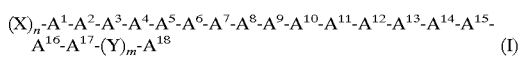

wherein
$A^1$ is missing or is a small or lipophilic amino acid or phenylpropionic acid, which optionally is acylated, such as acetylated, $A^2$ is an aromatic, lipophilic or small amino acid, and is optionally acylated, such as acetylated, when $A^1$ is missing, $A^3$ is a small or lipophilic or polar amino acid, or $A^2$–$A^3$ represent 5-aminopentanoic acid, N-Me-antranilic acid, 4-aminocyclohexane carboxylic acid or 3-aminomethylbenzoic acid, $A^4$ is a small or an aromatic amino acid, or $A^3$–$A^4$ represent N-Me-antranilic acid, $A^5$ is a lipophilic or polar amino acid, $A^6$ is a small or polar or lipophilic amino acid, $A^7$ is a small or polar or lipophilic amino acid, $A^8$ is a polar amino acid or (L or D)-Ala, $A^9$ is a lipophilic or polar amino acid, $A^{10}$ is a lipophilic or polar amino acid, $A^{11}$ is a lipophilic or polar amino acid, $A^{12}$ is a polar or lipophilic amino acid or missing, $A^{13}$ is a polar or lipophilic amino acid or missing, $A^{14}$ is a lipophilic or polar amino acid or missing, $A^{15}$ is a lipophilic or polar amino acid or missing, $A^{16}$ is a small or polar amino acid or missing, $A^{17}$ is a small or polar amino acid or missing, $A^{18}$ is OH or $NH_2$, X is a polar, a lipophilic, an aromatic or a small amino acid, Y is a polar, a lipophilic, an aromatic or a small amino acid, n+m is zero or an integer from 1–82, or two or more of $A^1$ to $A^7$, X and Y may independently of each other be a cyclisation amino acid, in which case one or more bridges may be formed, said bridges being selected from disulphide, lactame and Gly-lactame bridges; or a pharmaceutically acceptable salt thereof, provided that there is at least two simultaneous amino acid modifications relative to the nociceptin sequence or an unnatural amino acid in position $A^1$.

In the above compound of formula 1, the amino acids are selected from natural as well as unnatural amino acids, which may have either L- or D-configuration. Throughout this specification no indication before the amino acid means L-configuration.

Although the individual moities $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, X and Y in the compound of formula I are indicated as amino acids, it is immediately apparent that each of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, X and Y are joined by peptide bonds so as to constitute the compound of formula I.

In the above compound of formula I there is at least two simultaneous amino acid modifications relative to the nociceptin sequence or an unnatural amino acid in position $A^1$. Said modifications should comprise any substitution, addition, deletion and/or insertion of a natural or unnatural amino acid relative to the nociceptin sequence. Preferably there are from 2 to 15 simultaneous amino acid modifications relative to the nociceptin sequence or an unnatural amino acid in position $A^1$. More preferred there are from 2 to 13, such as 2, 3, 4, 5, 6, 7, 8, 9, 10, 11, 12 or 13 modifications relative to the nociceptin sequence or an unnatural amino acid in position $A^1$.

In one embodiment of the compound of formula I $A^1$ is a small amino acid such as Ala, D-Ala, Gly, Sar, Aib or βAla, which optionally is acylated, such as acetylated. In a particular embodiment $A^1$ is Ala, D-Ala, Gly, which optionally is acylated, in particular acetylated. In a more particular embodiment $A^1$ is Ac-Ala, Ala or Gly. In an even more particular embodiment $A^1$ is Ala or Gly.

The term "Ac" indicates that the designated amino acid is acetylated.

In another embodiment of the compound of formula I $A^1$ is a lipophilic amino acid such as Phe, Trp, 1Nal, 2Nal, Tyr, Leu, Val, Ile, Met, Nleu, Ala, 3-Amb, Abu, N-Me-Phe, homo-Phe (or hPhe), Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclo-hexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof, which optionally is acylated, such as acetylated. In a particular embodiment $A^1$ is Ala, D-Ala, 3-Amb, Abu, D-Abu, Phe, D-Phe, Tyr, D-Tyr, homo-Phe, D-homo-Phe, NMe-Phe, D-NMe-Phe, 2Nal, D-2Nal, Leu, D-Leu, Val, D-Val, Ile, D-Ile, Met, D-Met, Phg, D-Phg, NLeu, D-NLeu, N-Bzl-Gly, Tic or D-Tic, which optionally is acylated, e.g. acetylated. In a more particular embodiment $A^1$ is Ala, Ac-Phe, Phe, NMe-Phe, Phg, Leu, 2Nal, N-Bzl-Gly, 3-Amb, Tic and homo-Phe.

In a further embodiment of the compound of formula I $A^1$ is phenylpropionic acid.

In a still further embodiment of the compound of formula I $A^1$ is missing.

In a still further embodiment of the compound of formula I $A^2$ is an aromatic amino acid, such as Phe, Trp, 1Nal, 2Nal, Tyr, His, N-Me-Phe, homo-Phe, Tic, Phg, Pyridyl-Ala, thienyl-Ala, Bip, Dip, Indolin-2-carboxylic acid, Tetrahydronorharmancarboxylic acid or N-Bzl-Gly, as well as the D-configurations hereof. In a particular embodiment $A^2$ is Phe, D-Phe, 1Nal, D-1 Nal, 2Nal or D-2Nal. In a more particular embodiment $A^2$ is D-2Nal.

In a further embodiment of the compound of formula I $A^2$ is a lipophilic amino acid, such as Phe, Trp, 1Nal, 2Nal, Tyr, Leu, Val, Ile, Met, Nleu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^2$ is Ala, D-Ala, Phe, D-Phe, 1Nal, D-1Nal, 2Nal, D-2Nal, Pro, D-Pro, Cys, D-Cys, Pen or D-Pen. In a more particular embodiment $A^2$ is Ala, D-Pro, Cys, D-Cys, D-Pen, D-2Nal and D-Ala.

In a still further embodiment of the compound of formula I $A^2$ is a small amino acid, such as Ala, D-Ala, Gly, Sar, Aib, or βAla. In a particular embodiment $A^2$ is Ala, D-Ala, Gly or Sar. In a more particular embodiment $A^2$ is Gly, Sar, Ala and D-Ala.

In a further embodiment of the compound of formula I $A^2$ is a cyclisation amino acid, such as Cys, Pen, Asp, Dap, Lys, Glu, Orn, homo-Cys, Dab, N-$C_{1-6}$alkylamino-Gly or N-$C_{1-6}$alkylcarboxy-Gly, as well as the D-configurations hereof. In a particular embodiment $A^2$ is Cys, D-Cys, Pen, D-pen, Asp or D-Asp. In a more particular embodiment $A^2$ is Cys, D-Cys, D-Pen or D-Asp.

In a further embodiment of the compound of formula I $A^1$ is missing and $A^2$ is an acylated aromatic, lipophilic, small or cyclisation amino acid. In a particular embodiment $A^2$ is a small amino acid which is acylated, preferably acetylated. In a more particular embodiment $A^2$ is Ac-Gly.

In a further embodiment of the compound of formula I $A^3$ is a small amino acid such as Ala, D-Ala, Gly, Sar, Aib, or βAla. In a particular embodiment $A^3$ is Gly, Ala, D-Ala, Sar or Aib. In a more particular embodiment $A^3$ is Ala, Gly, Sar or Aib.

In a still further embodiment of the compound of formula I $A^3$ is a lipophilic amino acid such as Phe, Trp, 1Nal, 2Nal, Tyr, Leu, Val, Ile, Met, Nleu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^3$ is Phe, D-Phe, Ala, D-Ala, Aib, Cys or D-Cys. In a more particular embodiment $A^3$ is Ala, Phe, Aib, Cys or D-Cys.

In a further embodiment of the compound of formula I $A^3$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^3$ is Thr, D-Thr, Asp or D-Asp. In a more particular embodiment $A^3$ is Thr, Asp and D-Asp. In an even ore particular embodiment $A^3$ is Asp and D-Asp.

In a still further embodiment of the compound of formula I $A^3$ is a cyclisation amino acid, such as Cys, Pen, Asp, Dap, Lys, Glu, Orn, homo-Cys, Dab, N-$C_{1-6}$alkylamino-Gly or N-$C_{1-6}$alkylcarboxy-Gly, as well as the D-configurations hereof. In a particular embodiment $A^3$ is Cys, D-Cys, Asp or D-Asp.

In a further embodiment of the compound of formula I $A^4$ is a small amino acid such as Ala, D-Ala, Gly, Sar, Aib or βAla. In a particular embodiment $A^4$ is Ala, D-Ala or Gly. In a more particular embodiment $A^4$ is Ala or Gly. In an even more particular embodiment $A^4$ is Ala.

In a further embodiment of the compound of formula I $A^4$ is a an aromatic amino acid such as Phe, Trp, 1Nal, 2Nal, Tyr, His, N-Me-Phe, homo-Phe, Tic, Phg, Pyridyl-Ala, thienyl-Ala, Bip, Dip, Indolin-2-carboxylic acid, Tetrahydronorharmancarboxylic acid or N-Bzl-Gly, as well as the D-configurations hereof. In a particular embodiment $A^4$ is Phe, D-Phe, N-Me-Phe, N-Me-D-Phe, Tic or D-Tic. In a more particular embodiment $A^4$ is Phe, N-Me-Phe and Tic.

In a further embodiment of the compound of formula I $A^5$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^5$ is Ala, D-Ala, Val, D-Val, Abu, D-Abu, Leu, D-Leu, Met, D-Met, NLeu, D-NLeu, Cys, D-Cys, Pen or D-pen. In a more particular embodiment $A^5$ is Ala, Val, Cys, D-Cys, Abu or Pen.

In a still further embodiment of the compound of formula I $A^5$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^5$ is Thr, D-Thr, Arg, D-Arg. In a more particular embodiment $A^5$ is Thr, Arg or D-Arg.

In a still further embodiment of the compound of formula I $A^5$ is a cyclisation amino acid such as Cys, Pen, Asp, Dap, Lys, Glu, Orn, homo-Cys, Dab, N-alkylamino-Gly or N-alkylcarboxy-Gly, as well as the D-configurations hereof. In a particular embodiment $A^5$ is Cys, D-Cys, Pen, D-pen, Dap or D-Dap. In a more particular embodiment $A^5$ is Cys, D-Cys, Pen and Dap.

In a further embodiment of the compound of formula I $A^6$ is a small amino acid such as Ala, D-Ala, Gly, Sar, Aib or βAla. In a particular embodiment $A^6$ is Gly, Ala or D-Ala. In a more particular embodiment $A^6$ is Gly or Ala.

In a still further embodiment of the compound of formula I $A^6$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^6$ is Arg, D-Arg, Lys, D-Lys, Asp or D-Asp. In a more particular embodiment $A^6$ is Arg, D-Arg, Lys and Asp.

In a further embodiment of the compound of formula I $A^6$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^6$ is Pro, D-Pro, Ala, D-Ala, Cys or D-Cys. In a more particular embodiment $A^6$ is Pro, Ala, Cys or D-Cys.

In a still further embodiment of the compound of formula I $A^6$ is a cyclisation amino acid such as Cys, Pen, Asp, Dap, Lys, Glu, Orn, homo-Cys, Dab, N-$C_{1-6}$alkylamino-Gly or N-$C_{1-6}$alkylcarboxy-Gly, as well as the D-configurations hereof. In a particular embodiment $A^6$ is Cys, D-Cys, Lys, D-Lys, Asp or D-Asp. In a more particular embodiment $A^6$ is Cys, D-Cys, Lys and Asp.

In a further embodiment of the compound of formula I $A^7$ is a small amino acid such as Ala, D-Ala, Gly, Sar, Aib or βAla. In a particular embodiment $A^7$ is Ala, D-Ala or Aib. In a more particular embodiment $A^7$ is Ala or Aib.

In a still further embodiment of the compound of formula I $A^7$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^7$ is Arg, D-Arg, Ser, D-Ser, Lys, D-Lys, Asp or D-Asp. In a more particular embodiment $A^7$ is Arg, Ser, Lys or Asp.

In a further embodiment of the compound of formula I $A^7$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^7$ is Ala, D-Ala, Aib, Cys or D-Cys. In a more particular embodiment $A^7$ is Ala, Aib, Cys or D-Cys. In an even more particular embodiment $A^7$ is Ala, Aib or D-Cys.

In a still further embodiment of the compound of formula I $A^7$ is a cyclisation amino acid such as Cys, Pen, Asp, Dap, Lys, Glu, Orn, homo-Cys, Dab, N-$C_16$alkylamino-Gly or N-$C_{1-6}$alkylcarboxy-Gly, as well as the D-configurations hereof. In a particular embodiment $A^7$ is Lys, D-Lys, Cys, D-Cys, Asp or D-Asp. In a more particular embodiment $A^7$ is Cys, D-Cys, Lys and Asp. In an even more particular embodiment $A^7$ is D-Cys, Lys and Asp.

In a further embodiment of the compound of formula I $A^8$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^8$ is Arg, D-Arg, Ser, D-Ser, Thr, D-Thr, His, D-His, homo-Arg, D-homo-Arg, Citrulline (Abbrevation Cit), Lys or D-Lys. In a more particular embodiment $A^8$ is Arg, Ser, Lys, Thr, homo-Arg, Cit or His.

In a still further embodiment of the compound of formula I $A^8$ is (L or D)-Ala. In a particular embodiment $A^8$ is Ala.

In a preferred embodiment of the compound of formula I $A^8$ is Arg.

In a still further embodiment of the compound of formula I $A^9$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^9$ is Leu, D-Leu, Ala or D-Ala. In a more particular embodiment $A^9$ is Ala or Leu.

In a further embodiment of the compound of formula I $A^9$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^9$ is Arg, D-Arg, Lys, D-Lys, Ser or D-Ser. In a more particular embodiment $A^9$ is Arg, Lys or Ser.

In a still further embodiment of the compound of formula I $A^9$ is a cyclisation amino acid such as Cys, Pen, Asp, Dap, Lys, Glu, Orn, homo-Cys, Dab, N-C$_{1-6}$alkylamino-Gly or N-C$_{1-6}$alkylcarboxy-Gly, as well as the D-configurations hereof. In a particular embodiment $A^9$ is Lys, D-Lys, Dap or D-Dap. In a particular embodiment $A^9$ is Lys or Dap.

In a further embodiment of the compound of formula I $A^{10}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{10}$ is Aib, Leu, D-Leu, Ala, D-Ala, Cys or D-Cys. In a more particular embodiment $A^{10}$ is Aib, Ala, Leu or Cys.

In a still further embodiment of the compound of formula I $A^{10}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{10}$ is Ser, D-Ser, Arg, D-Arg, Lys, D-Lys, Orn or D-Orn. In a more particular embodiment $A^{10}$ is Ser, Arg, Lys or Orn.

In a further embodiment of the compound of formula I $A^{10}$ is a cyclisation amino acid such as Cys, Pen, Asp, Dap, Lys, Glu, Orn, homo-Cys, Dab, N-C$_{1-6}$alkylamino-Gly or N-C$_{1-6}$alkylcarboxy-Gly, as well as the D-configurations hereof. In a particular embodiment $A^{10}$ is Lys, D-Lys, Cys, D-Cys, Orn or D-Orn. In a particular embodiment $A^{10}$ is Lys, Cys and Orn.

In a further embodiment of the compound of formula I $A^{11}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{11}$ is Ala, D-Ala, Leu, D-Leu, Aib, Cys or D-Cys. In a more particular embodiment $A^{11}$ is Ala, Leu, Aib, Cys or D-Cys.

In a further embodiment of the compound of formula I $A^{11}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{11}$ is Arg, D-Arg, Lys, D-Lys, Ser, D-Ser, Orn or D-Orn. In a more particular embodiment $A^{11}$ is Arg, Lys, Ser or Orn.

In a further embodiment of the compound of formula I $A^{11}$ is a cyclisation amino acid such as Cys, Pen, Asp, Dap, Lys, Glu, Orn, homo-Cys, Dab, N-C$_{1-6}$alkylamino-Gly or N-C$_{1-6}$alkylcarboxy-Gly, as well as the D-configurations hereof. In a particular embodiment $A^{11}$ is Lys, D-Lys, Cys, D-Cys, Orn or D-Orn. In a more particular embodiment $A^{11}$ is Lys, Cys, D-Cys and Orn.

In a still further embodiment of the compound of formula I $A^{12}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{12}$ is Lys, D-Lys, Arg, D-Arg, Ser or D-Ser. In a more particular embodiment $A^{12}$ is Lys, Arg or Ser.

In a further embodiment of the compound of formula I $A^{12}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{12}$ is Leu, D-Leu, Ala or D-Ala. In a more particular embodiment $A^{12}$ is Ala or Leu.

In a still further embodiment of the compound of formula I $A^{12}$ is missing.

In a further embodiment of the compound of formula I $A^{12}$ is a cyclisation amino acid such as Cys, Pen, Asp, Dap, Lys, Glu, Orn, homo-Cys, Dab, N-C$_{1-6}$alkylamino-Gly or N-C$_{1-6}$alkylcarboxy-Gly, as well as the D-configurations hereof. In a particular embodiment $A^{12}$ is Lys or D-Lys. In a more particular embodiment $A^{12}$ is Lys.

In a still further embodiment of the compound of formula I $A^{13}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{13}$ is Lys, D-Lys, Asn, D-Asn, Glu or D-Glu. In a more particular embodiment $A^{13}$ is Asn, Lys or Glu.

In a further embodiment of the compound of formula I $A^{13}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{13}$ is Ala, D-Ala, Leu or D-Leu. In a more particular embodiment $A^{13}$ is Ala or Leu.

In a still further embodiment of the compound of formula I $A^{13}$ is a cyclisation amino acid such as Cys, Pen, Asp, Dap, Lys, Glu, Orn, homo-Cys, Dab, N-C$_{1-6}$alkylamino-Gly or N-C$_{1-6}$alkylcarboxy-Gly, as well as the D-configurations hereof. In a particular embodiment $A^{13}$ is Lys, D-Lys, Glu or D-Glu. In a more particular embodiment $A^{13}$ is Lys or Glu.

In a further embodiment of the compound of formula I $A^{13}$ is a missing.

In a still further embodiment of the compound of formula I $A^{14}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{14}$ is Ala, D-Ala, Leu, D-Leu, Tyr, D-Tyr, Phe or D-Phe. In a more particular embodiment $A^{14}$ is Ala, Leu, Tyr or Phe.

In a further embodiment of the compound of formula I $A^{14}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{14}$ is Asn, D-Asn, Gln, D-Gln, Tyr or D-Tyr. In a more particular embodiment $A^{14}$ is Asn, Gln or Tyr.

In a still further embodiment of the compound of formula I $A^{14}$ is missing.

In a further embodiment of the compound of formula I $A^{15}$ is a lipophilic amino acid such as Phe, Trp, 1Nal, 2Nal, Tyr, Leu, Val, Ile, Met, NLeu, Ala, 3-Amb, Abu, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid or 1-aminocyclooctancarboxylic acid, as well as the D-configurations hereof. In a particular embodiment $A^{15}$ is Ala, D-Ala or Aib. In a more particular embodiment $A^{15}$ is Ala or Aib.

In a still further embodiment of the compound of formula I $A^{15}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{15}$ is Asn, D-Asn, Gln or D-Gln. In a more particular embodiment $A^{15}$ is Asn or Gln.

In a further embodiment of the compound of formula I $A^{15}$ is missing.

In a still further embodiment of the compound of formula I $A^{16}$ is a small amino acid such as Ala, D-Ala, Gly, Sar, Aib or βAla. In a particular embodiment $A^{16}$ is Ala or D-Ala. In a more particular embodiment $A^{16}$ is Ala.

In a further embodiment of the compound of formula I $A^{16}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{16}$ is Asn, D-Asn, Gln, D-Gln, Lys or D-Lys. In a more particular embodiment $A^{16}$ is Asn, Gln or Lys.

In a still further embodiment of the compound of formula I $A^{16}$ is a cyclisation amino acid such as Cys, Pen, Asp, Dap, Lys, Glu, Orn, homo-Cys, Dab, N-$C_{1-6}$alkylamino-Gly or N-$C_{1-6}$alkylcarboxy-Gly, as well as the D-configurations hereof. In a particular embodiment $A^{16}$ is Lys or D-Lys. In a more particular embodiment $A^{16}$ is Lys.

In a further embodiment of the compound of formula I $A^{17}$ is missing.

In a still further embodiment of the compound of formula I $A^{17}$ is a small amino acid such as Ala, D-Ala, Gly, Sar, Aib or βAla. In a particular embodiment $A^{17}$ is Ala or D-Ala. In a more particular embodiment $A^{17}$ is Ala.

In a further embodiment of the compound of formula I $A^{17}$ is a polar amino acid such as Ser, His, Thr, Gln, Asp, Glu, Lys, Arg, Orn, Asn, Tyr, homo-Arg, Cit or Pyridyl-Ala, as well as the D-configurations hereof. In a particular embodiment $A^{17}$ is Gln, D-Gln, His or D-His. In a more particular embodiment $A^{17}$ is Gln or His.

In a still further embodiment of the compound of formula I $A^{17}$ is missing.

In a further embodiment of the compound of formula I $A^{18}$ is OH.

In a still further embodiment of the compound of formula I $A^{18}$ is $NH_2$.

In a further embodiment of the compound of formula I $A^2$–$A^3$ represents 5-aminoentanoic acid, N-Me-antranilic acid, 4-aminocyclohexanecarboxylic acid or 3-aminomethylbenzoic acid.

In a still further embodiment of the compound of formula I $A^3$–$A^4$ represents N-Me-antranilic acid.

In a further embodiment of the compound of formula I n+m is 0–12, preferably 0–6, more preferred 0–3, most preferred n+m is zero.

In a still further embodiment of the compound of formula I two or more of $A^1$ to $A^{17}$, X and Y may independently of each other be a cyclisation amino acid, in which case one or two bridges may be formed, said bridges being selected from disulphide, lac-tame and Gly-lactame bridges, and the cyclisation amino acid is selected from Cys, D-Cys, Pen, D-Pen, Asp, D-Asp, Dap, D-Dap, Lys, D-Lys, Glu, D-Glu, Orn, D-Orn, homo-Cys, Dab, D-Dab, N-$C_{1-6}$alkylamino-Gly and N-$C_{1-6}$alkylcarboxy-Gly. Preferably disulphide bridges in the compound of formula I are formed between position $A^i$ and $A^{i+3}$ wherein i is an integer selected from 1–14, and/or between position $A^j$ and $A^{j+6}$ wherein j is an integer selected from 1–11. Preferably lactame bridges in the compound of formula I are formed between position $A^k$ and $A^{k+3}$ wherein k is an integer selected from 1–14, and/or between position $A^l$ and $A^{l+7}$ wherein l is an integer selected from 1–10, and/or between position $A^p$ and $A^{p+6}$ wherein p is an integer selected from 1–11. Preferably Gly-lactame bridges in the compound of formula I are formed between position $A^q$ and $A^{q+4}$ wherein q is an integer selected from 1–13.

In a further embodiment of the compound of formula I a disulphide bridge is formed between position $A^i$ and $A^{i+3}$ wherein i is 2, 3, 6 or 7, preferably 2, 3 or 7. Preferably $A^i$ and $A^{i+3}$ are independently selected from Cys, D-Cys, D-Pen and Pen. In a particular embodiment disulphide bridges are DCys-DCys, Cys-Cys, Cys-DCys, DCys-Cys, DPen-Pen, D-Cys-Pen, D-Pen-Cys wherein i is 2, DCys-DCys, Cys-Cys, Cys-DCys, DCys-Cys wherein i is 3, and DCys-Cys wherein i is 7.

In a still further embodiment of the compound of formula I a disulphide bridge is formed between position $A^j$ and $A^{j+6}$ wherein j is 3 or 5, preferably 5. Preferably $A^j$ and $A^{j+6}$ are independently selected from Cys and D-Cys. In a particular embodiment disulphide bridges are DCys-DCys, Cys-Cys, Cys-DCys, DCys-Cys, wherein j is 5.

In a further embodiment of the compound of formula I a lactame bridge is formed between position $A^k$ and $A^{k+3}$ wherein k is 2, 3, 6 or 7, preferably 2. Preferably $A^k$ and $A^{k+3}$ are independently selected from D-Asp, Lys and Dap. In a particular embodiment lactame bridge is D-Asp-Dap wherein k is 2.

In a still further embodiment of the compound of formula I a lactame bridge is formed between position $A^l$ and $A^{l+7}$ wherein l is 2 or 3, preferably 2. Preferably $A^l$ and $A^{l+7}$ are independently selected from D-Asp, Lys and Asp. In a particular embodiment lactame bridges are DAsp-Lys wherein l is 2.

In a further embodiment of the compound of formula I a lactame bridge is formed between position $A^p$ and $A^{p+6}$ wherein p is 3 or 5, preferably 3. Preferably $A^p$ and $A^{p+6}$ are independently selected from Asp, D-Asp, Lys and Dap. In a particular embodiment lactame bridge is DAsp-Dap, Asp-Lys or D-Asp-Lys wherein p is 3.

In a still further embodiment of the compound of formula I a Gly-lactame bridge is formed between position $A^q$ and $A^{q+4}$ wherein q is 2, 3, 5, 6 or 7, preferably 6 or 7. Preferably $A^q$ and $A^{q+4}$ are independently selected from Asp and Orn. In a particular embodiment Gly-lactame bridge is Asp-Gly-Orn wherein q is 6, and Asp-Gly-Orn wherein q is 7.

In a further embodiment of the compound of formula I two bridges are formed which bridges are selected among the above embodiments of disulphide, lactame and Gly-lactame bridges. In one embodiment there is a disulphide bridge and a Gly-lactame bridge. A particular embodiment is a D-Cys-Cys disulphide bridge wherein i is 2, together with a Asp-Gly-Orn Gly-lactame bridge wherein q is 6.

Specifically preferred compounds of the invention are:

| Sequence | ID |
|---|---|
| A-G-G-F-T-G-A-R-K-S-A-R-K-L-A-N-Q-NH$_2$ | (SEQ ID NO. 1) |
| F-A-G-F-T-G-A-R-K-S-A-R-K-L-A-N-Q-NH$_2$ | (SEQ ID NO: 2) |
| F-G-A-F-T-G-A-R-K-S-A-R-K-L-A-N-Q-NH$_2$ | (SEQ ID NO: 3) |
| F-G-G-A-T-G-A-R-K-S-A-R-K-L-A-N-Q-NH$_2$ | (SEQ ID NO: 4) |
| F-G-G-F-A-G-A-R-K-S-A-R-K-L-A-N-Q-NH$_2$ | (SEQ ID NO: 5) |
| F-G-G-F-T-A-A-R-K-S-A-R-K-L-A-N-Q-NH$_2$ | (SEQ ID NO: 6) |
| F-G-G-F-T-G-A-A-K-S-A-R-K-L-A-N-Q-NH$_2$ | (SEQ ID NO: 7) |
| F-G-G-F-T-G-A-R-A-S-A-R-K-L-A-N-Q-NH$_2$ | (SEQ ID NO: 8) |
| F-G-G-F-T-G-A-R-K-A-A-R-K-L-A-N-Q-NH$_2$ | (SEQ ID NO: 9) |
| F-G-G-F-T-G-A-R-K-S-A-A-K-L-A-N-Q-NH$_2$ | (SEQ ID NO: 10) |
| F-G-G-F-T-G-A-R-K-S-A-R-A-L-A-N-Q-NH$_2$ | (SEQ ID NO: 11) |
| F-G-G-F-T-G-A-R-K-S-A-R-K-A-A-N-Q-NH$_2$ | (SEQ ID NO: 12) |
| F-G-G-F-T-G-A-R-K-S-A-R-K-L-A-A-Q-NH$_2$ | (SEQ ID NO: 13) |
| F-G-G-F-T-G-A-R-K-S-A-R-K-L-A-A-A-NH$_2$ | (SEQ ID NO: 14) |
| F-G-G-F-T-G-A-R-K-S-A-A-A-L-A-N-Q-NH$_2$ | (SEQ ID NO: 15) |
| G-G-F-T-G-A-R-K-S-A-R-K-L-A-N-Q-OH | (SEQ ID NO: 16) |
| Ac-F-G-G-F-T-G-A-R-K-S-A-R-K-L-A-N-Q-OH | (SEQ ID NO: 17) |
| Ac-G-G-F-T-G-A-R-K-S-A-R-K-L-A-N-Q-OH | (SEQ ID NO: 18) |
| (N-Me-Phe)-G-G-F-T-G-A-R-K-S-A-R-K-L-A-N-Q-OH | (SEQ ID NO: 19) |
| (Phg)-G-G-F-T-G-A-R-K-S-A-R-K-L-A-N-Q-OH | (SEQ ID NO: 20) |
| (hPhe)-G-G-F-T-G-A-R-K-S-A-R-K-L-A-N-Q-OH | (SEQ ID NO: 21) |
| Phenylpropionyl-G-G-F-T-G-A-R-K-S-A-R-K-L-A-N-Q-OH | (SEQ ID NO: 22) |
| (2Nal)-G-G-F-T-G-A-R-K-S-A-R-K-L-A-N-Q-OH | (SEQ ID NO: 23) |
| (N-Bzl-Gly)-G-G-F-T-G-A-R-K-S-A-R-K-L-A-N-Q-OH | (SEQ ID NO: 24) |
| (Tic)-G-G-F-T-G-A-R-K-S-A-R-K-L-A-N-Q-OH | (SEQ ID NO: 25) |
| (3-Amb)-G-G-F-T-G-A-R-K-S-A-R-K-L-A-N-Q-OH | (SEQ ID NO: 26) |
| L-G-G-F-T-G-A-R-K-S-A-R-K-L-A-N-Q-OH | (SEQ ID NO: 27) |
| F-(Sar)-T-G-A-R-K-S-A-R-K-L-A-N-Q-NH$_2$ | (SEQ ID NO: 28) |
| F-a-G-F-T-G-A-R-K-S-A-R-K-L-A-N-Q-NH$_2$ | (SEQ ID NO: 29) |
| F-(5-Apent)-A-R-K-S-A-R-K-L-A-N-Q-NH$_2$ | (SEQ ID NO: 30) |
| F-(N-Me anthranilic acid)-F-T-G-A-R-K-S-A-R-K-L-A-N-Q-NH$_2$ | (SEQ ID NO: 31) |
| F-(4-Aminocyclohexane-carboxylic acid)-F-T-G-A-R-K-S-A-R-K-L-A-N-Q-NH$_2$ | (SEQ ID NO: 32) |
| F-(3-Amb)-F-T-G-A-R-K-S-A-R-K-L-A-N-Q-NH$_2$ | (SEQ ID NO: 33) |
| F-p-G-F-T-G-A-R-K-S-A-R-K-L-A-N-Q-NH$_2$ | (SEQ ID NO: 34) |
| F-G-(Sar)-F-T-G-A-R-K-S-A-R-K-L-A-N-Q-NH$_2$ | (SEQ ID NO: 35) |
| F-G-(Aib)-F-T-G-A-R-K-S-A-R-K-L-A-N-Q-NH$_2$ | (SEQ ID NO: 36) |
| F-G-G-(N-Me-Phe)-T-G-A-R-K-S-A-R-K-L-A-N-Q-NH$_2$ | (SEQ ID NO: 37) |
| F-G-G-(Tic)-T-G-A-R-K-S-A-R-K-L-A-N-Q-OH | (SEQ ID NO: 38) |
| F-G-(N-Me anthranilic acid)-T-G-A-R-K-S-A-R-K-L-A-N-Q-NH$_2$ | (SEQ ID NO: 39) |
| F-G-G-F-(Abu)-G-A-R-K-S-A-R-K-L-A-N-Q-NH$_2$ | (SEQ ID NO: 40) |
| F-G-G-F-(Val)-G-A-R-K-S-A-R-K-L-A-N-Q-OH | (SEQ ID NO: 41) |
| F-G-G-F-T-P-A-R-K-S-A-R-K-L-A-N-Q-NH$_2$ | (SEQ ID NO: 42) |
| F-G-G-F-T-G-A-K-K-S-A-R-K-L-A-N-Q-NH$_2$ | (SEQ ID NO: 43) |
| F-G-G-F-T-G-A-H-K-S-A-R-K-L-A-N-Q-NH$_2$ | (SEQ ID NO: 44) |
| F-G-G-F-T-G-A-Cit-K-S-A-R-K-L-A-N-Q-NH$_2$ | (SEQ ID NO: 45) |
| F-G-G-F-T-G-A-R-K-S-A-R-K-Y-A-N-Q-NH$_2$ | (SEQ ID NO: 46) |
| F-G-G-F-R-G-A-T-K-S-A-R-K-L-A-N-Q-NH$_2$ | (SEQ ID NO: 47) |
| F-G-G-F-r-G-A-T-K-S-A-R-K-L-A-N-Q-NH$_2$ | (SEQ ID NO: 48) |
| F-G-G-F-T-r-A-A-K-S-A-R-K-L-A-N-Q-NH$_2$ | (SEQ ID NO: 49) |
| A-(D-2Nal)-G-F-T-G-A-R-K-S-A-R-K-L-A-N-Q-NH$_2$ | (SEQ ID NO: 50) |
| F-a-G-F-T-A-(Aib)-R-S-L-(Aib)-S-E-F-(Aib)-K-H-NH$_2$ | (SEQ ID NO: 51) |

(SEQ ID NO: 52)
F-c-G-F-c-G-A-R-K-S-A-R-K-L-A-N-Q-NH$_2$ (disulfide bridge between the two c residues)

(SEQ ID NO: 53)
F-C-G-F-C-G-A-R-K-S-A-R-K-L-A-N-Q-NH$_2$ (disulfide bridge between the two C residues)

(SEQ ID NO: 54)
F-c-G-F-C-G-A-R-K-S-A-R-K-L-A-N-Q-NH$_2$ (disulfide bridge between c and C)

(SEQ ID NO: 55)
F-c-G-F-(Pen)-G-A-R-K-S-A-R-K-L-A-N-Q-NH$_2$ (disulfide bridge between c and Pen)

(SEQ ID NO: 56)
F-(D-Pen)-G-F-C-G-A-R-K-S-A-R-K-L-A-N-Q-NH$_2$ (disulfide bridge between D-Pen and C)

(SEQ ID NO: 57)
F-(D-Pen)-G-F-(Pen)-G-A-R-K-S-A-R-K-L-A-N-Q-NH$_2$ (disulfide bridge between D-Pen and Pen)

-continued

F-C-G-F-c-G-A-R-K-S-A-R-K-L-A-N-Q-NH₂ (bond between C at position 2 and c at position 5) (SEQ ID NO: 58)

F-G-C-F-T-C-A-R-K-S-A-R-K-L-A-N-Q-NH₂ (bond between C at position 3 and C at position 6) (SEQ ID NO: 59)

F-G-C-F-T-c-A-R-K-S-A-R-K-L-A-N-Q-NH₂ (SEQ ID NO: 60)

F-G-c-F-T-C-A-R-K-S-A-R-K-L-A-N-Q-NH₂ (SEQ ID NO: 61)

F-G-c-F-T-c-A-R-K-S-A-R-K-L-A-N-Q-NH₂ (SEQ ID NO: 62)

F-G-G-F-C-G-A-R-K-S-C-R-K-L-A-N-Q-NH₂ (SEQ ID NO: 63)

F-G-G-F-C-G-A-R-K-S-c-R-K-L-A-N-Q-NH₂ (SEQ ID NO: 64)

F-G-G-F-c-G-A-R-K-S-C-R-K-L-A-N-Q-NH₂ (SEQ ID NO: 65)

F-G-G-F-c-G-A-R-K-S-c-R-K-L-A-N-Q-NH₂ (SEQ ID NO: 66)

F-G-G-F-T-G-c-R-K-C-A-R-K-L-A-N-Q-NH₂ (SEQ ID NO: 67)

F-(D-Asp)-G-F-(Dap)-G-A-R-K-S-A-R-K-L-A-N-Q-NH₂ (SEQ ID NO: 68)

F-(D-Asp)-G-F-T-K-A-R-K-S-A-R-K-L-A-N-Q-NH₂ (SEQ ID NO: 69)

F-G-(Asp)-F-T-G-K-R-K-S-A-R-K-L-A-N-Q-NH₂ (SEQ ID NO: 70)

F-G-(D-Asp)-F-T-G-K-R-K-S-A-R-K-L-A-N-Q-NH₂ (SEQ ID NO: 71)

F-G-(D-Asp)-F-T-G-A-R-(Dap)-S-A-R-K-L-A-N-Q-NH₂ (SEQ ID NO: 72)

F-G-G-F-T-D-A-R-K-(Orn)-A-R-K-L-A-N-Q-NH₂ (with (Gly) bridge) (SEQ ID NO: 73)

F-G-G-F-T-D-A-R-K-(Orn)-A-NH₂ (with (Gly) bridge) (SEQ ID NO: 74)

F-G-G-F-T-G-D-R-K-S-Orn-R-K-L-A-N-Q-NH₂ (with (Gly) bridge) (SEQ ID NO: 75)

-continued

F-c-G-F-C-D-A-R-K-Orn-A-R-K-L-A-N-Q-NH$_2$ (SEQ ID NO: 76)

In the above structural formulas and throughout the present specification, the following terms have the indicated meaning:

The term "nociceptin sequence" as used herein has the formula H-Phe-Gly-Gly-Phe-Thr-Gly-Ala-Arg-Lys-Ser-Ala-Arg-Lys-Leu-Ala-Asn-Gln-OH.

The term "aromatic amino acid" is intended to comprise any natural as well as unnatural amino acids comprising an aromatic moity, such as Phe, Trp, 1Nal, 2Nal, Tyr, His, N-Me-Phe, homo-Phe, Tic, Phg, Pyridyl-Ala, thienyl-Ala, Bip, Dip, Indolin-2-carboxylic acid, Tetrahydronorharman-carboxylic acid, N-Bzl-Gly and the like.

The term "small amino acid" is intended to comprise the amino acids selected from Gly, Ala, D-Ala, Sar, Aib and βAla.

The term "Lipophilic amino acid" is intended to comprise any natural as well as unnatural amino acids comprising a lipophilic moity, such as Phe, 3-Amb, Abu, Trp, 1Nal, 2Nal, Tyr, Leu, Val, Ile, Met, Nleu, Ala, N-Me-Phe, homo-Phe, Tic, Pro, Phg, Aib, Bip, Dip, Tetrahydronorharmancarboxylic acid, Guvacin, N-Bzl-Gly, Nip, Cyclohexyl-Ala, Cys, Pen, 1-aminocyclohexancarboxylic acid, 1-aminocyclopentancarboxylic acid, 1-aminocyclobutancarboxylic acid, 1-aminocyclopropancarboxylic acid, 1-aminocycloheptancarboxylic acid, 1-aminocyclooctancarboxylic acid and the like.

The term "Polar amino acid" is intended to comprise any natural as well as unnatural amino acids comprising a polar moity, such as Ser, His, Thr, Gln, Asp, Glu, Lys, Arg, Orn, Asn, Tyr, Pyridyl-Ala, homo-Arg, Cit and the like.

The term "cyclisation amino acid" is intended to comprise any natural as well as unnatural amino acids being able to form a disulphide, lactame or Gly-lactame bridge, such as e.g. Cys, Pen, Asp, Dap, Lys, Glu, Orn, homo-Cys, Dab, N-C$_{1-6}$alkylamino-Gly, N-C$_{1-6}$alkylcarboxy-Gly and the like.

The term "disulphide bridge" is intended to mean that two cyclisation amino acids, such as e.g. Cys, D-Cys, Pen and/or D-Pen, are linked together via the bridge —S—S—.

The term "lactame bridge" is intended to mean that two cyclisation amino acids, such as e.g. Asp, D-Asp, Dap, D-Dap, Lys and/or D-Lys, are linked together via the bridge —C(=O)—NH— or —HN—C(=O)—.

The term "Gly-lactame bridge" is intended to mean that two cyclisation amino acids, such as e.g. Asp, D-Asp, Orn and/or D-Orn, are linked together via the bridge —C(=O)—NH—CH$_2$—C(=O)—NH— or —HN—C(=O)—CH$_2$—NH—C(=O)—.

Certain of the above defined terms may occur more than once in the above formula I, and upon such occurence each term shall be defined independently of the other.

Abbreviations used:

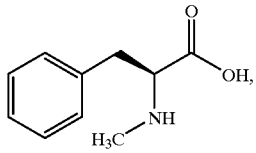

N-Me-Phe (N-methyl phenylalanine)

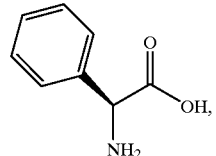

Phg (Phenylglycine)

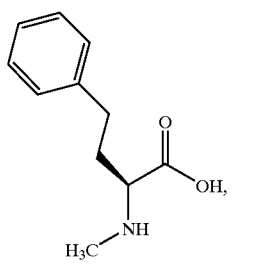

hPhe (homo-phenylalanine)

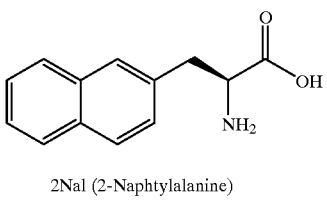

2Nal (2-Naphtylalanine)

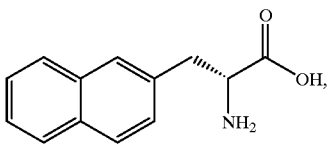

D2Nal (D-2-Naphtylalanine)

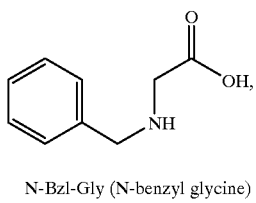

N-Bzl-Gly (N-benzyl glycine)

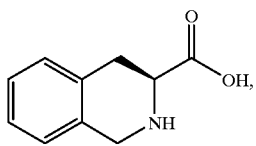

Tic (1,2,3,4 tetrahydroisoquinoline-3-carboxylic acid)

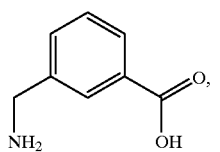
3Amb (3-aminomethylbenzoic acid)

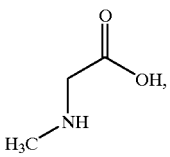
Sar (Sarcosine)

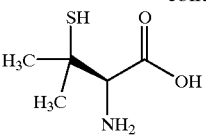
Pen (Penicillamine)

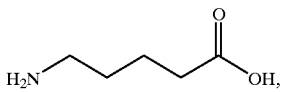
5Apent (5 aminopentanoic acid)

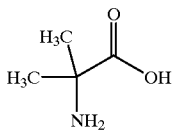
Aib (aminoisobutyric acid)

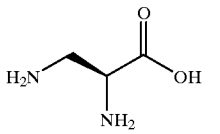
Dap (2,3-diaminopropionic acid)

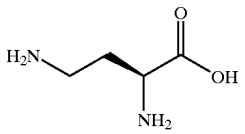
Dap (2,3-diaminobutyric acid)

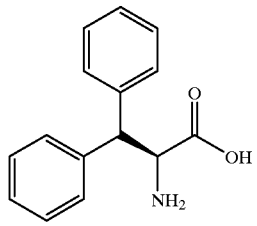
Dip (diphenylalanine)

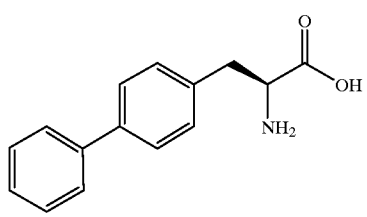
Bip (biphenylalanine)

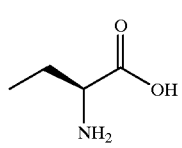
Abu (α-aminobutyric acid)

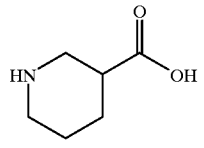
Nip (nipecotic acid (R,S))

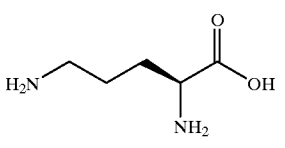
Orn (Ornithine)

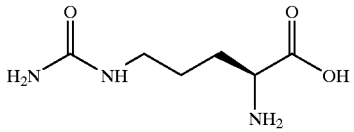
Cit (Citruline)

Where 3-letter codes or where non standard amino acid residues are incorporated into a sequence of standard 1 letter amino acid abbreviations they are enclosed in parenthesis.

Sequences of standard 1 letter amino acid abbreviations are all assumed to have a free amino terminal unless where a specific acyl function is indicated. A C-terminal carboxyl is indicated with —OH and a C-terminal carboxamide is indicated with —NH$_2$.

The compounds of the present invention may have one or more asymmetric centres and it is intended that stereoisomers (optical isomers), as separated, pure or partially purified stereoisomers or racemic mixtures thereof are included in the scope of the invention.

Within the present invention, the compounds of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

The compounds of the above general formula I are useful for the preparation of a pharmaceutical composition for the treatment of vasomotor disturbances, in particular the peripheral vasomotor effects known as hot flushes or hot flashes. Throughout the present specicfication treatment is meant to comprise profylactic treatment as well.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

The invention also relates to a method of preparing the above mentioned compounds, which method is described in the experimental part.

The compounds of formula I are useful for antagonising physiologic effects of an opioid in an animal, and for treating/preventing a disease related to: hyperalgesia, neuroendocrine secretion, stress, locomotor activity, anxiety, instinctive behaviour, decreasing of learning, memory, curiosity, attention and/or sensory perception.

Pharmaceutical Compositions

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington: The Science and Practise of Pharmacy*, 19$^{th}$ Ed. 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human, such as a woman, in need of such treatment, prevention, elimination, alleviation or amelioration of various diseases as mentioned above and especially vasomotor disturbances, in particular the peripheral vasomotor effects known as hot flushes or hot flashes. Such mammals include also animals, both domestic animals, e.g. household pets, and non-domestic animals such as wildlife.

The compounds of the invention are effective over a wide dosage range. For example, in the treatment of adult human patients, dosages from about 0.05 to about 1000 mg, preferably from about 0.1 to about 100 mg, per day may be used. A most preferable dosage is about 0.1 mg to about 70 mg per day. In choosing a regimen for patients, it may frequently be necessary to begin with a dosage of from about 20 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject (mammal) to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula I admixed with a pharmaceutically acceptable carrier or diluent.

In a further aspect, the present invention relates to a method of treating vasomotor disturbances, in particular the peripheral vasomotor effects known as hot flushes or hot flashes.

In a still further aspect, the present invention relates to a method of treating the physiologic effects of an opioid in an animal, and a disease related to: hyperalgesia, neuroendocrine secretion, stress, locomotor activity, anxiety, instinctive behaviour, decreasing of learning, memory, curiosity, attention and/or sensory perception.

In a still further aspect, the present invention relates to the use of one or more compounds of the general formula I or pharmaceutically acceptable salts thereof for the preparation of a medicament for the treatment of vasomotor disturbances, in particular the peripheral vasomotor effects known as hot flushes or hot flashes.

Any novel feature or combination of features described herein is considered essential to this invention.

Biological Methods

The pharmacological properties of the compounds of the invention can be illustrated by determining their ability to compete for Nociceptin binding to receptors expressed in brain.

Detailed conditions for the In Vitro Assay of Nociceptin Receptor Binding are described as follows:

The peptide Nociceptin has been identified as the endogenous ligand of the ORL-1 receptor that is expressed in brain (Menieur et al., Nature (1995) 377, 532–535; Reinscheid et al., Science (1995) 270, 792–795). As Nociceptin is commercially available in a radiolabeled form the ORL-1 receptors present in brain can be identified by measuring the specific binding of [leucyl-$^3$H]Nociceptin to brain membranes. The affinity of a test substance for the ORL-1 receptor can then be determined by measuring its ability to compete for the specific [leucyl-$^3$H]Nociceptin binding.

All membrane preparation steps are performed at 0–4° C. Freshly dissected rat brain (minus cerebellum) is homogenized with a teflon Dounce homogenizer in tissue preparation buffer (25 mM $KH_2PO_4$, pH 7.4, containing 0.32M Sucrose, 0.15 M KCL and 5 mM EDTA) and centrifuged at 5000 rpm (Sorvall RC5B, SS-34 rotor) for 10 min. This washed pellet is then homogenized in the tissue preparation buffer using a Ultra-Torex homogenizer and centrifuged at 15,000 rpm for 10 min. The final pellet is homogenized with a teflon Dounce homogenizer in tissue preparation buffer and frozen at −80° C. in 1 ml aliquots.

On the day of the assay, membranes are thawed at room temperature, diluted 1:10 (v/v) in assay buffer (25 mM $KH_2PO_4$, pH 7.4) and washed by centrifuging for 10 min at 16,000 rpm. The pellet is then re-homogenized with a teflon Dounce homogenizer in assay buffer containing protease inhibitors (50 mg/ml bacitracin, 10 mg/ml captropril, 5 mg/ml bestatin, 0.5 mg/ml thiorphan). The assay reaction is carried out in 96-well plates. To initiate the assay the tissue and test substance are mixed and [leucyl-$^3$H]Nociceptin (Amersham) is added; this mixture is then incubated at 25° C. for 60–90 min. At the end of the incubation the reaction mixture is filtered through Packard Unifilter GF/B filterplates using a Packard Filtermate 196 cell harvester. The filterplate is dried and 50 $\mu$l of Packard Microscint 20 scintillation counting solution added to each filter. Radioactivity present on the filters is then measured by Beta-scintillation counting on a Packard Top Counter.

Non-specific binding is evaluated by including Nociceptin (1 $\mu$M) in the assay instead of test substance. Data were fit to competition curves and analyzed using non-linear least squares fitting procedures. Results were recorded as $K_i$ values.

EXAMPLES

The process for preparing compounds of formula I and preparations containing them is further illustrated in the following examples, which however, are not to be construed as limiting.

Abbrevations:
TLC: thin layer chromatography
DMSO: dimethylsulfoxide
$CDCl_3$: deutorated chloroform
DMF: N, N-dimethylformamide
min: minutes
h: hours Example 1

[D-Ala$^2$] Nociceptin(1–17)-amide

F-a-G-F-T-G-A-R-K-S-A-R-K-L-A-N-Q-NH$_2$ 1.a The protected peptidyl resin Fmoc-Phe-Thr(Bu$^t$)-Gly-Ala-Arg(Pmc)-Lys(Boc)-Ser(Bu$^t$)-Ala-Arg(Pmc)-Lys(Boc)-Leu-Ala-Asn(Trt)-Gln(Trt)-(Rink resin) was synthesized according to the Fmoc strategy on an Applied Biosystems 431A peptide synthesizer in 0.25 mmol scale using the manufacturer supplied FastMoc UV protocols which employ HBTU ( 2-(1H-Benzotriazol-1-yl-)-1,1,3, 3tetramethyluronium hexafluorophosphate) mediated couplings in NMP (N-methyl pyrrolidone) and UV monitoring of the deprotection of the Fmoc protection group. The starting resin used for the synthesis was 559 mg (4-((2', 4'-dimethoxyphenyl)-(Fmoc-amino)methyl)-phenoxy resin (Rink resin) (Novabiochem, Bad Soden, Germany. cat. #: 01-64-0013 ) with a substitution capacity of 0.45 mmol/g. The protected amino acid derivatives used were Fmoc-Phe-OH, Fmoc-Thr(But)-OH, Fmoc-Gly-OH, Fmoc-Ala-OH, Fmoc-Arg(Pmc)-OH, Fmoc-Lys(Boc)-OH, Fmoc-Ser(Bug-OH, Fmoc-Leu-OH, Fmoc-Asn(Trt)-OH, Fmoc-Gln(Trt)-OH. Resulting in 1333 mg peptidyl resin.

1.b The synthesis was continued as above using 292 mg (0.054 mmol) of the peptide resin resulting from (1.a) and coupling with Fmoc-Gly-OH, Fmoc-D-Ala-OH and Fmoc-Phe-OH. This resulted in 245 mg of the protected peptide resin H-Phe-D-Ala-Gly-Phe-Thr(Bu$^t$)-Gly-Ala-Arg(Pmc)-Lys(Boc)-Ser(But-Ala-Arg(Pmc)-Lys(Boc)-Leu-Ala-Asn(Trt)-Gln(Trt)-(Rink resin).

1.c The peptide was cleaved from 245 mg of the protected peptidyl resin obtained from (1.b) by stirring for 180 min at room temperature with a mixture of trifluoro acetic acid (TFA) (2 ml), phenol (150 mg), ethanedithiol (50 $\mu$l), thioanisole (100 $\mu$l) and water (100 $\mu$l). The cleavage mixture was filtered and the filtrate was concentrated to approximately 0.5 ml by a stream of nitrogen. The crude peptide was precipitated from this oil with 49 ml diethyl ether and washed 3 times with 50 ml diethyl ether.

1.d The crude peptide was dried and purified by semi-preparative HPLC on a 25 mm×250 mm column packed with 7$\mu$ C-18 silica which was preequilibrated with 15% $CH_3CN$ in 0.1% TFA in water. The crude peptide was dissolved in 2 ml 70% $CH_3CN$/0.1% TFA in $H_2O$ and diluted to 200 ml with $H_2O$. This solution was divided into two equal portions and one was injected on the column. The column was eluted at 40° C. with a gradient of 15%–26% $CH_3CN$ in 0.1% TFA in water at ml/min during 47 min. The peptide containing fractions were collected and the peptide isolated from the pool by lyophilisation after dilution with water.

1.e The final product obtained was characterized by RP-HPLC/Ion spray mass spectrometry (LC-MS) (retention time and molecular mass) and by analytical RP-HPLC (retention time and peptide amount). The peptide amount was calculated by comparing the UV detector response with that of a Nociceptin standard where the amount had been determined by amino acid analysis. The RP-HPLC analysis was performed using UV detection at 214 nm and a Vydac 218TP54 4.6 mm×250 mm 5µ C-18 silica column (The Separations Group, Hesperia) which was eluted at 1 ml/min at 42° C. Two different elution conditions were used:

A1: The column was equilibrated with 5% $CH_3CN$ in a buffer consisting of 0.1 M $(NH_4)_2SO_4$, which was adjusted to pH 2.5 with 4M $H_2SO_4$ and eluted by a gradient of 5% to 60% $CH_3CN$ in the same buffer during 50 min.

B1: The column was equilibrated with 5% $CH_3CN/0.1\%$ $TFA/H_2O$ and eluted by a gradient of 5% $CH_3CN/0.1\%$ $TFA/H_2O$ to 60% $CH_3CN/0.1\%$ $TFA/H_2O$ during 50 min.

The retention times using elution conditions A1 and B1 was found to be 19.37 min and 19.20 min, respectively and the peptide yield to be 28 mg.

The LC-MS analysis was performed using UV detection at 214 nm and a Symmetry 3.0 mm×150 mm 5µ C-18 silica column (Waters, Milford Mass., USA) which was eluted at 1 ml/min room temperature. It was equilibrated with 5% $CH_3CN/0.1\%$ $TFA/H_2O$ and eluted by a gradient of 5% $CH_3CN/0.1\%$ $TFA/H_2O$ to 90% $CH_3CN/0.1\%$ $TFA/H_2O$ during 15 min and then re-equilibrated for 5 min. In addition to the UV detection a fraction of the column eluate was introduced into the ionspray interface of an PE-Sciex API 100 mass spectrometer. The mass range 300–3000 amu was scanned for every 2 seconds during the elapse of the chromatography. Using these conditions the retention time of the product as determined from the UV trace, was found to be 5.91 min and the molecular mass was found to 1822.4 amu which is in agreement with the expected structure within the experimental error of the method (i 1 amu).

Example 2

[Phe$^1$] Nociceptin(1–17)-amide (hPhe)-G-G-F-T-G-A-R-K-S-A-R-K-L-A-N-Q-NH$_2$

The protected peptidyl resin H-Gly-Gly-Phe-Thr(But)-Gly-Ala-Arg(Pmc)-Lys(Boc) Ser(But)-Ala-Arg(Pmc)-Lys(Boc)-Leu-Ala-Asn(Trt)-Gln(Trt)-(Wang) was synthesized according to the Fmoc strategy in 0.25 mmol scale using procedures described in example 1.a from 446 mg Fmoc-Gln(Trt)-Wang resin (Novabiochem, Bad Soden, Germany. cat. #: 04-12-2036 ) with a substitution capacity of 0.57 mmol/g. The last residue was attached manually to 120 mg of this protected peptide resin by coupling for 20 h at room temperature with the the preformed HOBT ester which was formed by reacting Boc-hPhe-OH (0.2 mmol, 56 mg) with HOBT (0.2 mmol, 31 mg) and EDAC (0.2 mmol, 38 mg) in DMF (3 ml) for 15 min. After the preactivation the mixture was added to the resin and DIEA (0.2 mmol, 34 µl) was added. Then the resin was sequentialy washed with DMF, DCM, DMF, Isopropanol, methanol and diethylether (5 ml each) and the peptide was cleaved and the crude peptide purified and characterized using procedures similar to those in Example 1.c, 1.d and 1.e. By LC-MS retention time and molecular mass was found to 6.02 min and 1822.8 amu (theor. 1823.1) respectively. By analytical HPLC retention times for condition A1 and B1 was found to be 18.95 min and 19.40 min respectively.

Example 3

[Ala$^1$] Nociceptin(1–17)-amide

A-G-G-F-T-G-A-R-K-S-A-R-K-L-A-N-Q-NH$_2$ 3.a The protected peptidyl resin Fmoc-Ala-Gly-Gly-Phe-Thr(Bu$^t$)-Gly-Ala-Arg(Pmc) Lys(Boc)-Ser(Bu$^t$)-Ala-Arg(Pmc)-Lys(Boc)-Leu-Ala-Asn(Trt)-Gln(Trt)-(Rink resin) was synthesized according to the Fmoc strategy on an Abimed 422 multiple peptide synthesizer in 0.025 mmol scale using the 48 cartridge valve block. In each cartridge was put 58 mg Rink resin with a substitution capacity of 0.45 mmol/g. The synthesis protocol used is outlined below.

1. Swell resin in 2×1 ml DMF (dimethylformamide)
2. Deprotect 2×5 min., each with 3 ml 20% piperidine in DMF.
3. Wash 6× with 1.5 ml DMF
4. Add:
   4 equivalents of Fmoc protected amino acid derivative in 150 µl NMP (N-methyl pyrrolidone).
   4 equivalents of PyBOP benzotriazole-1-yl-oxy-tris-pyrrolidinophosphonium hexafluorophosphate) in 110 µl NMP
   4 equivalents of 1-methyl morpholine in 50 µl DMF
5. Coupling for 20–60 min.
6. Addition of 1 ml DCM (dichloromethane)
7. Coupling for 10–30 min.
8. Wash 6× with 1.5 ml DMF
9. Repeat from step 2 if chain elongation is not finished or else skip to next.
10. Deprotect 2×5 min., each with 3 ml 20% piperidine in DMF.
11. Wash 6× with 1.5 ml DMF
12. Wash 3× with 1.5 ml DCM
13. Dry resin in vacuum.

The protected amino acid derivatives used for one cartridge were Fmoc-Ala-OH, Fmoc-Gly-OH, Fmoc-Thr(Bu$^t$)-OH, Fmoc-Ala-OH, Fmoc-Arg(Pmc)-OH, Fmoc-Lys(Boc)-OH, Fmoc-Ser(Bu$^t$)-OH, Fmoc-Leu-OH, Fmoc-Asn(Trt)-OH, Fmoc-Gln(Trt)-OH.

After the chain elongation the peptide was cleaved from the protected peptidyl resin obtained, the crude peptide purified and the final product characterized using procedures similar to those in Example 1.c, 1.d and 1.e. By LC-MS retention time and molecular mass was found to 6.12 min and 1732 amu (theor. 1732,8) respectively. By analytical HPLC retention times for condition A1 and B1 was found to be 16.60 min and 20.20 min respectively.

Example 4

(Abimed, Rink, —S—S—)

[D-Cys$^2$, Cys$^5$] Nociceptin(1–17)-amide

F-c-G-F-T-C-A-R-K-S-A-R-K-L-A-N-Q-NH$_2$ 4.a The protected peptidyl resin Fmoc-Phe-D-Cys(Acm)-Phe-Thr(Bu)-Cys(Acm)-Ala-Arg(Pmc)-Lys(Boc)-Ser(Bu$^t$)-Ala-Arg(Pmc)-Lys(Boc)-Leu-Asn(Trt)-Gln(Trt)-(Rink resin) was synthesized according to the Fmoc strategy on an Abimed 422 multiple peptide synthesizer in 0.025 mmol scale using procedures similar to those in example 3.a.

4.b After the chain elongation the peptide was cleaved from the protected peptidyl resin obtained from (2.a) by stirring for 180 min at room temperature with a mixture of trifluoro acetic acid (TFA) (2 ml), phenol (150 mg) and water (100 µl). The cleavage mixture was filtered and the filtrate was concentrated to approximately 0.5 ml by a stream of nitrogen. The crude peptide was precipitated from this oil with 49 ml diethyl ether and washed 3 times with 50 ml diethyl ether and dried.

4.c The dry precipitate was dissolved in 8 ml water and the peptide content was estimated by HPLC analysis (1.e) to 20 mg≅10 μmol. Then 1.5 equivalents HCl (15 μl, 1 M hydrochloric acid) and 20 equivalents iodine (50 mg) dissolved in 23 ml acetic acid was added and the mixture was stirred for 3 hours. After this the excess iodine was reduced by addition zinc dust (250 mg) and stirring was continued until the solution turned colorless (15 min) and the remaining zink was removed by filtration and the filtrate concentrated in vacuum to an oil on a rotary evaporator.

4.d This oil was redissolved in 100 ml water and the peptide purified and characterized in analogy with (1.d) and (i.e.) By LC-MS retention time and molecular mass was found to 6.8 min and 1854.4 amu (theor. 1854.2) respectively. By analytical HPLC retention times for condition A1 and B1 was found to be 18.58 min and 20.28 min respectively.

Example 5

Cyclo 6–10 [Asp(Gly)$^6$, Orn$^{10}$] Nociceptin(1–17)-amide

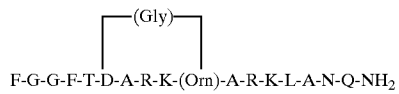

F-G-G-F-T-D-A-R-K-(Orn)-A-R-K-L-A-N-Q-NH$_2$ 5.a The protected peptidyl resin Boc-Orn(Fmoc)-Ala-Arg(TOS)-Lys(CI-Z)-Leu-Ala-Asn-Gln-(MBHA resin) was synthesized according to the Boc strategy on an Applied Biosystems 430A peptide synthesizer in 0.50 mmol scale using slightly modified manufacturer supplied protocols. For coupling is used 1 mmol of the preformed symmetrical anhydrides which are prepared from 2 mmol of the N-protected amino acid derivative by reaction 1 mmol N, N'-dicyclohexylcarbodiimide (DCC) in DCM for approximately 8 min. In cases where protected amino acid derivatives having a low solubility in DCM, or undergoing side reactions during symmetrical anhydride formation, are to be introduced, an alternative activation procedure is used. Then the amino acid derivatives are coupled as preformed 1-hydroxybenzotriazole esters. This is for example the case with Boc-Arg(TOS)-OH, Boc-Asn-OH, Boc-Orn(Fmoc)-OH, Boc-Asp(OFm)-OH and Boc-Gln-OH. The 1-hydroxybenzotriazole esters are formed in DMF by reaction of 2 mmol of the protected amino acid derivative with 2 mmol 1-hydroxybenzotriazole and 2 mmol DCC for approximately 33 min. For N-deprotection during chain elongation is used approximately 50% TFA acid in DCM. After deprotection and wash the resin is neutralized by two diisopropylethylamine/DMF washings. Then it is washed further and then coupled with a DMF solution of the activated amino acid residue. The resin used for the synthesis was 728 mg (4-methylbenzhydrylamine resin) (MBHA resin) (Saxon Biochemicals GMBH, Hannover, Germany, Cat# RMIS50) with a substitution capacity of 0.49 mmol/g and the protected amino acid derivatives used were Boc-Orn(Fmoc)-OH, Boc-Ala-OH, Boc-Arg(TOS)-OH, Boc-Lys(CI-Z)-OH, Boc-Ala-OH, Boc-Leu-OH, Boc-Asn-OH, Boc-Gln-OH resulting in 896 mg peptidyl resin.

5.b The sidechain protection on Orn of this protected peptidyl resin was deprotected by treatment with 20% piperidine/DMF (25 ml, 15 min) and after sequential wash with DMF, DCM, DMF, Isopropanol, methanol and diethylether (5 ml each) the side chain was coupled for 3 hours in DMF (10 ml) with Fmoc-Gly-OH (594 mg, 4 eq.) using 1-Ethyl-3-(3'-dimethylaminopropyl) carbodiimide•HCl (EDAC) (384 mg, 4 eq.) as coupling reagent with the addition of 1-hydroxybenzotriazole (HOBT) (306 mg, 4 eq.) and DIEA (3421μl, 4 eq.). Then the resin was washed again as above and after drying the yield was 921 mg resin.

5.c This resin (477 mg, 0.25 mmol) was then loaded into the 430A synthesizer and elongated to Boc-Asp(OFm)-Ala-Arg(TOS)-Lys(CI-Z)-Orn(Fmoc-Gly)-Ala-Arg(TOS)-Lys(CI-Z)-Leu-Asn-Gln-(MBHA resin) by coupling with Boc-Asp(OFm)-OH, Boc-Ala-OH, Boc-Arg(TOS)-OH, Boc-Lys(CI-Z)-OH. Then the side chain protection of Asp and the N-protection of Gly was removed by treatment with 20% piperidine/DMF (25 ml, 15 min) and sequentialy washed with DMF, 10% DIEA/DMF, DMF, DCM, DMF, Isopropanol, methanol and diethylether (5 ml each). The resulting free carboxylic acic and the amino group of the Gly were linked to each other through an amide bond by coupling for 72 h in DMF (10 ml) with EDAC (192 mg, 4 eq.) as coupling reagent with the addition of HOBT (153 mg, 4 eq.) and DIEA (171 μ, 4 eq.). After sequential wash as above and drying the yield was 457 mg.

5.d Finally the chain elongation of the resin was finished on the 430A synthesizer to give

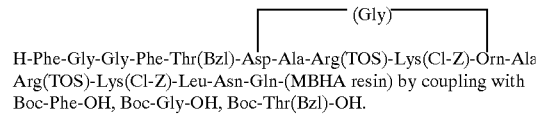

H-Phe-Gly-Gly-Phe-Thr(Bzl)-Asp-Ala-Arg(TOS)-Lys(Cl-Z)-Orn-Ala Arg(TOS)-Lys(Cl-Z)-Leu-Asn-Gln-(MBHA resin) by coupling with Boc-Phe-OH, Boc-Gly-OH, Boc-Thr(Bzl)-OH.

5.e Finally the peptide was deprotected and cleaved from the resin by stirring for 75 min at 0° C. with a mixture of liquid HF (5 ml) and m-cresol (0.5 ml). After this the HF was evaporated at 0° C. by a stream of nitrogen and the peptide was precipitated from the remaining oil together with the spend resin by addition of diethyl ether (50 ml). The precipitate was washed 2 times with diethyl ether (50 ml) and after drying the peptide is extracted from the precipitate with water and purified and characterized in analogy with example 1.d and 1.e. By LC-MS retention time and molecular mass was found to 6.75 min and 1932.8 amu (theor. 1932.2) respectively. By analytical HPLC retention times for condition A1 and B1 was found to be 21.32 min and 20.35 min respectively.

Example 6

[N-Me-Phe$^4$] Nociceptin(1–17)-amide

F-G-G-(N-Me-Phe)-T-G-A-R-K-S-A-R-K-L-A-N-Q-NH$_2$

The peptide resin H-Phe-Gly-Gly-N-Me-Phe-Thr(Bu)-Gly-Ala-Arg(Pmc)-Lys(Boc)-Ser(Bu$^t$)-Ala-Arg(Pmc)-Lys(Boc)-Leu-Asn(Trt)-Gln(Trt)-(Rink resin) was synthesized using procedures similar to those in example 1 with the exception that residue 3. (Gly) was coupled to the less reactive residue 4. (N-Me-Phe) using, O-(7-Azabenzotriazol-1-yl)-1,1,3,3 tetramethyluronium hexafluorophosphate (HATU) as the coupling reagent. For the coupling was used 4 equivalents of the amino acid residue and 4 equivalents of the activation reagent. Coupling was performed in presence of 7 equivalents of DIEA. (Coupling with HATU is used for coupling on residues which have an amino group with low reactivity, typicaly N-alkylated amino acids. It is also used for coupling of residues, and onto residues which are sterically hindered for example α,α branched amino acids.) After the chain elongation the peptide was cleaved from the protected peptidyl resin obtained, the crude peptide purified and the final product characterized using procedures similar to those in Example 1.c, 1.d and 1.e. By LC-MS retention time and molecular mass was found to 5.88 min and 1822.8 amu (theor. 1822 amu.) respectively. By analytical HPLC retention times for condition A1 and B1 was found to be 18.00 min and 19.00 min respectively.

Example 7

[D-Cys$^7$, Cys$^{10}$] Nociceptin(1–17)-amide

F-G-G-F-T-G-c-R-K-C-A-R-K-L-A-N-Q-NH$_2$

The protected peptide resin H-Phe-Gly-Gly-Phe-Thr (But)-Gly-D-Cys(Acm)-Arg(Pmc)-Lys(Boc)-Cys(Acm)-Ala-Arg(Pmc)-Lys(Boc)-Leu-Ala-Asn(Trt)-Gln(Trt)-(Rink resin) was synthesized according to the Fmoc strategy on an Applied Bio-systems 431A peptide synthesizer in 0.25 mmol scale from 507 mg Rink resin with a substitution of 0.45 mmol/g using procedures similar to those in example 1.a. Then the peptide H-Phe-Gly-Gly-Phe-Thr-Gly-D-Cys (Acm)-Arg-Lys-Cys(Acm)-Ala-Arg-Lys-Leu-Ala-Asn-Gln-NH$_2$ was cleaved from the protected peptidyl resin and subsequently oxidized to H-Phe-Gly-Gly-Phe-Thr-Gly-D-Cys-Arg-Lys-Cys-Ala-Arg-Lys-Leu-Ala-Asn-Gln-NH$_2$ in analogy to example 4.b and 4.c This product was finally purified and characterised in analogy with example 1.d and 1.e. By LC-MS retention time and molecular mass was found to 5.97 min and 1854.0 amu (theor. 1854.3 amu.) respectively. By analytical HPLC retention times for condition A1 and B1 was found to be 19.45 min and 19.53 min respectively.

Examples 8–53

| | | | RP-HLPC a) | | LC-MS analysis b) | |
|---|---|---|---|---|---|---|
| | | Prepared in | | | mass | theoretical |
| Ex. | Peptide | analogy to example: | A1 (min) | B1 (min) | min. | found (amu.) | mass (amu.) |
| 8 | F-A-G-F-T-G-A-R-K-S-A-R-K-L-A-N-Q-NH$_2$ | 3. | 17.7 | 18.4 | 6.28 | 1822.8 | 1822 |
| 9 | F-G-A-F-T-G-A-R-K-S-A-R-K-L-A-N-Q-NH$_2$ | 3. | 17.6 | 20.5 | 6.31 | 1821.6 | 1822 |
| 10 | F-G-G-A-T-G-A-R-K-S-A-R-K-L-A-N-Q-NH$_2$ | 3. | 13.6 | 14.4 | 5.67 | 1732.8 | 1732 |
| 11 | F-G-G-F-A-G-A-R-K-S-A-R-K-L-A-N-Q-NH$_2$ | 3. | 17.6 | 18.2 | 6.3 | 1777.6 | 1778 |
| 12 | F-G-G-F-T-A-A-R-K-S-A-R-K-L-A-N-Q-NH$_2$ | 3. | 18.6 | 19.2 | 6.45 | 1821.2 | 1822 |
| 13 | F-G-G-F-T-G-A-A-K-S-A-R-K-L-A-N-Q-NH$_2$ | 3. | 19.5 | 19.6 | 6.72 | 1722.4 | 1723 |
| 14 | F-G-G-F-T-G-A-R-A-S-A-R-K-L-A-N-Q-NH$_2$ | 3. | 18.0 | 18.9 | 6.47 | 1750.4 | 1751 |
| 15 | F-G-G-F-T-G-A-R-K-A-A-R-K-L-A-N-Q-NH$_2$ | 3. | 19.7 | 19.46 | 6.61 | 1792.4 | 1791 |
| 16 | F-G-G-F-T-G-A-R-K-S-A-A-K-L-A-N-Q-NH$_2$ | 3. | 18.7 | 20.1 | 6.49 | 1722.0 | 1723 |
| 17 | F-G-G-F-T-G-A-R-K-S-A-R-A-L-A-N-Q-NH$_2$ | 3. | 18.5 | 20.4 | 6.68 | 1750.4 | 1751 |
| 18 | F-G-G-F-T-G-A-R-K-S-A-R-K-A-A-N-Q-NH$_2$ | 3. | 14.8 | 18.1 | 6.28 | 1765.6 | 1766 |
| 19 | F-G-G-F-T-G-A-R-K-S-A-R-K-L-A-A-Q-NH$_2$ | 3. | 18.3 | 20.1 | 6.62 | 1764.4 | 1765 |
| 20 | F-G-G-F-T-G-A-R-K-S-A-R-K-L-A-N-A-NH$_2$ | 3. | 18.3 | 20.2 | 6.64 | 1750.4 | 1751 |
| 21 | G-G-F-T-G-A-R-K-S-A-R-K-L-A-N-Q-OH | 2. | 14.1 | 14.6 | 5.52 | 1662.8 | 1662 |
| 22 | Ac-F-G-G-F-T-G-A-R-K-S-A-R-K-L-A-N-Q-OH | 2. | 20.2 | 21.4 | 6.39 | 1850.4 | 1851 |
| 23 | Ac-G-G-F-T-G-A-R-K-S-A-R-K-L-A-N-Q-OH | 2. | 15.5 | 16.3 | 5.11 | 1703.6 | 1704 |
| 24 | N-Me-Phe-G-G-F-T-G-A-R-K-S-A-R-K-L-A-N-Q-OH | 2. | 17.3 | 18.0 | 5.79 | 1822.1 | 1822 |
| 25 | Phg-G-G-F-T-G-A-R-K-S-A-R-K-L-A-N-Q-OH | 2. | 16.0 | 16.4 | 5.66 | 1795.1 | 1795 |
| 26 | Phenylpropionyl-G-G-F-T-G-A-R-K-S-A-R-K-L-A-N-Q-OH | 2. | 21.6 | 22.8 | 6.83 | 1794 | 1794 |
| 27 | (2Nal)-G-G-F-T-G-A-R-K-S-A-R-K-L-A-N-Q-OH | 2. | 20.7 | 21.4 | 6.54 | 1858.1 | 1858 |
| 28 | (N-Bzl-Gly)-G-G-F-T-G-A-R-K-S-A-R-K-L-A-N-Q-OH | 2. | 16.9 | 17.6 | 6.02 | 1808.1 | 1808 |
| 29 | (Tic)-G-G-F-T-G-A-R-K-S-A-R-K-L-A-N-Q-OH | 2. | 17.0 | 17.5 | 5.81 | 1820.8 | 1820 |
| 30 | (3Amb)-G-G-F-T-G-A-R-K-S-A-R-K-L-A-N-Q-OH | 2. | 15.6 | 16.1 | 5.90 | 1794.4 | 1794 |
| 31 | L-G-G-F-T-G-A-R-K-S-A-R-K-L-A-N-Q-OH | 2. | 16.6 | 17.2 | 6.26 | 1775.6 | 1775 |
| 32 | F-(Sar)-G-F-T-G-A-R-K-S-A-R-K-L-A-N-Q-NH$_2$ | 1. | 18.2 | 18.5 | 5.79 | 1822.8 | 1822 |
| 33 | F-(5Apent)-F-T-G-A-R-K-S-A-R-K-L-A-N-Q-NH$_2$ | 1. | 18.6 | 19.8 | 6.66 | 1792.4 | 1793 |
| 34 | F-(3Amb)-F-T-G-A-R-K-S-A-R-K-L-A-N-Q-NH$_2$ | 1. | 20.1 | 21.1 | 6.57 | 1827.6 | 1827 |
| 35 | F-p-G-F-T-G-A-R-K-S-A-R-K-L-A-N-Q-NH$_2$ | 1. | 20.3 | 20.4 | 6.79 | 1847.6 | 1848 |
| 36 | F-G-(Sar)-F-T-G-A-R-K-S-A-R-K-L-A-N-Q-NH$_2$ | 1. | 17.9 | 18.8 | 6.16 | 1822.8 | 1822 |
| 37 | F-G-(Aib)-F-T-G-A-R-K-S-A-R-K-L-A-N-Q-NH$_2$ | 1. | 19.6 | 20.3 | 657 | 1836.0 | 1836 |
| 38 | F-G-G-(Tic)-T-G-A-R-K-S-A-R-K-L-A-N-Q-OH | 2. | 16.9 | 18.1 | 6.51 | 1821.2 | 1821 |
| 39 | F-G-G-F-V-G-A-R-K-S-A-R-K-L-A-N-Q-OH | 2. | 17.9 | 18.9 | 6.54 | 1807.6 | 1807 |
| 40 | F-G-G-F-T-G-A-K-K-S-A-R-K-L-A-N-Q-NH$_2$ | 1. | 17.3 | 17.7 | 5.57 | 1779.6 | 1780 |
| 41 | F-G-G-F-T-G-A-R-K-S-A-R-K-Y-A-N-Q-OH | 2. | 15.9 | 17.1 | 5.64 | 1859 | 1859 |
| 42 | F-G-G-F-R-G-A-T-K-S-A-R-K-L-A-N-Q-NH$_2$ | 1. | 19.2 | 18.0 | 5.51 | 1807.2 | 1808 |
| 43 | A-(D-2Nal)-G-F-T-G-A-R-K-S-A-R-K-L-A-N-Q-NH$_2$ | 1. | 22.7 | 23.0 | 7.04 | 1872.6 | 1872 |
| 44 | F-a-G-F-T-A-(Aib)-R-S-L-Aib-S-E-F-(Aib)-K-H-NH$_2$ | 6. | 33.4 | 33.0 | 8.67 | 1852.4 | 1852 |

Examples 8–53 -continued

| Ex. | Peptide | Prepared in analogy to example: | RP-HLPC a) A1 (min) | B1 (min) | min. | LC-MS analysis b) mass found (amu.) | theoretical mass (amu.) |
|---|---|---|---|---|---|---|---|
| 45 | F-c-G-F-c-G-A-R-K-S-A-R-K-L-A-N-Q-NH₂ | 4. | 18.4 | 18.4 | 6.3 | 1853.2 | 1854 |
| 46 | F-C-G-F-C-G-A-R-K-S-A-R-K-L-A-N-Q-NH₂ | 4. | 18.2 | 19.7 | 6.18 | 1853.6 | 1854 |
| 47 | F-C-G-F-c-G-A-R-K-S-A-R-K-L-A-N-Q-NH₂ | 4. | 18.7 | 19.8 | 6.81 | 1854.4 | 1854 |
| 48 | F-G-G-F-C-G-A-R-K-S-C-R-K-L-A-N-Q-NH₂ | 7. | 16.3 | 18.1 | 6.28 | 1840.4 | 1840 |
| 49 | F-G-G-F-C-G-A-R-K-S-c-R-K-L-A-N-Q-NH₂ | 7. | 16.4 | 18.3 | 6.43 | 1839.6 | 1840 |
| 50 | F-G-G-F-c-G-A-R-K-S-C-R-K-L-A-N-Q-NH₂ | 7. | 16.3 | 18.2 | 6.03 | 1840.8 | 1840 |
| 51 | F-G-G-F-c-G-A-R-K-S-c-R-K-L-A-N-Q-NH₂ | 7. | 17.4 | 19.0 | 6.27 | 1839.6 | 1840 |
| 52 | F-G-G-F-T-D-A-R-K-(Orn)-A-NH₂ —(Gly)— | 5. | 16.6 | 17.3 | 6.18 | 1220.8 | 1221 |
| 53 | F-G-G-F-T-G-D-R-K-S-(Orn)-R-K-L-A-N-Q-NH₂ —(Gly)— | 5. | 15.4 | 16.9 | 6.08 | 1934 | 1934 | a) Retention times from RP-HPLC analysis using the conditions in example 1.e
b) Retention time and molecular mass from LC-MS analysis according to 1.e

---

We claim:

1. A method for the treatment of vasomotor disturbances, the method comprising administering to a subject in need thereof an effective amount of a compound of formula (I):

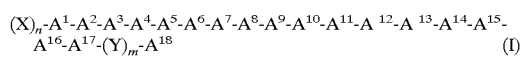

$(X)_n$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$(Y)_m$-$A^{18}$ (I)

wherein
- $A^1$ is missing or is a small or lipophilic amino acid or phenylpropionic acid, which optionally is acylated,
- $A^2$ is an aromatic, lipophilic or small amino acid, and is optionally acylated when $A^1$ is missing, as
- $A^3$ is a small or lipophilic or polar amino acid, or
- $A^2$–$A^3$ represent 5-aminopentanoic acid, N-Me-antranilic acid, 4-aminocyclohexane carboxylic acid or 3-aminomethylbenzoic acid,
- $A^4$ is a small or polar or an aromatic amino acid, or
- $A^3$–$A^4$ represent N-Me-antranilic acid.
- $A^5$ is a lipophilic or polar amino acid,
- $A^6$ is a small or polar or lipophilic amino acid,
- $A^7$ is a small or polar or lipophilic amino acid.
- $A^8$ is a polar amino acid or (L or D)-Ala.
- $A^9$ is a lipophilic or polar amino acid,
- $A^{10}$ is a lipophilic or polar amino acid,
- $A^{11}$ is a lipophilic or polar amino acid,
- $A^{12}$ is a polar or lipophilic amino acid or missing,
- $A^{13}$ is a polar or lipophilic amino acid or missing,
- $A^{14}$ is a polar or lipophilic amino acid or missing,
- $A^{15}$ is a polar or lipophilic amino acid or missing,
- $A^{16}$ is a small or polar amino acid or missing
- $A^{17}$ is a small or polar amino acid or missing
- $A^{18}$ is OH or $NH_2$,
- X is a polar, a lipophilic, an aromatic or a small amino acid,
- Y is a polar, a lipophilic, an aromatic or a small amino acid,
- n+m is zero or an integer from 1–82.
- or two or more of $A^1$ to $A^{17}$
  X and Y may independently of each other be a cyclisation amino acid, in which case one or more bridges may be formed, said bridges being selected from disulphide, lactame and Gly-lactame bridges; or a pharmaceutically acceptable salt thereof, provided that there is at least two simultaneous amino acid modifications relative to the nociceptin sequence or an unnatural amino acid in position $A^1$.

2. The method according to claim 1 wherein $A^1$ is a small amino acid, which optionally is acylated.

3. The method according to claim 1 wherein $A^1$ is a lipophilic amino acid, which optionally is acylated.

4. The method according to claim 1 wherein $A^1$ is phenylpropionic acid, which optionally is acylated.

5. The method according to claim 1 wherein $A^1$ is missing.

6. The method according to claim 1 wherein $A^2$ is an aromatic amino acid.

7. The method according to claim 1 wherein $A^2$ is a lipophilic amino acid.

8. The method according to claim 1 wherein $A^2$ is a small amino acid.

9. The method according to claim 1 wherein $A^2$ is a cyclisation amino acid.

10. The method according to claim 1 wherein $A^2$ is an acylated aromatic, lipophilic, small or cyclisation amino acid, preferably a small amino acid which is acetylated.

11. The method according to claim 1 wherein $A^3$ is a small amino acid.

12. The method according to claim 1 wherein $A^3$ is a lipophilic amino acid.

13. The method according to claim 1 wherein $A^3$ is a polar amino acid.

14. The method according to claim 1 wherein $A^3$ is a cyclisation amino acid.

15. The method according to claim 1 wherein $A^4$ is a small amino acid.

16. The method according to claim 1 wherein $A^4$ is an aromatic amino acid.

17. The method according to claim 1 wherein $A^5$ is a lipophilic amino acid.

18. The method according to claim 1 wherein $A^5$ is a polar amino acid.

19. The method according to claim 1 wherein $A^5$ is a cyclisation amino acid.

20. The method according to claim 1 wherein $A^6$ is a small amino acid.

21. The method according to claim 1 wherein $A^6$ is a polar amino acid.

22. The method according to claim 1 wherein $A^6$ is a lipophilic amino acid.

23. The method according to claim 1 wherein $A^6$ is a cyclisation amino acid.

24. The method according to claim 1 wherein $A^7$ is a small amino acid.

25. The method according to claim 1 wherein $A^7$ is a polar amino acid.

26. The method according to claim 1 wherein $A^7$ is a lipophilic amino acid.

27. The method according to claim 1 wherein $A^7$ is a cyclisation amino acid.

28. The method according to claim 1 wherein $A^8$ is a polar amino acid.

29. The method according to claim 28 wherein $A^8$ is Arg.

30. The method according to claim 1 wherein $A^8$ is (L or D)-Ala.

31. The method according to claim 1 wherein $A^9$ is a lipophilic amino acid.

32. The method according to claim 1 wherein $A^9$ is a polar amino acid.

33. The method according to claim 1 wherein $A^9$ is a cyclisation amino acid.

34. The method according to claim 1 wherein $A^{10}$ is a lipophilic amino acid.

35. The method according to claim 1 wherein $A^{10}$ is a polar amino acid.

36. The method according to claim 1 wherein $A^{10}$ is a cyclisation amino acid.

37. The method according to claim 1 wherein $A^{11}$ is a lipophilic amino acid.

38. The method according to claim 1 wherein $A^{11}$ is a polar amino acid.

39. The method according to claim 1 wherein $A^{11}$ is a cyclisation amino acid.

40. The method according to claim 1 wherein $A^{12}$ is a polar amino acid.

41. The method according to claim 1 wherein $A^{12}$ is a lipophilic amino acid.

42. The method according to claim 1 wherein $A^{12}$ is missing.

43. The method according to claim 1 wherein $A^{12}$ is a cyclisation amino acid.

44. The method according to claim 1 wherein $A^{13}$ is a polar amino acid.

45. The method according to claim 1 wherein $A^{13}$ is a lipophilic amino acid.

46. The method according to claim 1 wherein $A^{13}$ is a cyclisation amino acid.

47. The method according to claim 1 wherein $A^{13}$ is a missing.

48. The method according to claim 1 wherein $A^{14}$ is a lipophilic amino acid.

49. The method according to claim 1 wherein $A^{14}$ is a polar amino acid.

50. The method according to claim 1 wherein $A^{14}$ is missing.

51. The method according to claim 1 wherein $A^{15}$ is a lipophilic amino acid.

52. The method according to claim 1 wherein $A^{15}$ is a polar amino acid.

53. The method according to claim 1 wherein $A^{15}$ is missing.

54. The method according to claim 1 wherein $A^{16}$ is a small amino acid.

55. The method according to claim 1 wherein $A^{16}$ is a polar amino acid.

56. The method according to claim 1 wherein $A^{16}$ is a cyclisation amino acid.

57. The method according to claim 1 wherein $A^{16}$ is missing.

58. The method according to claim 1 wherein $A^{17}$ is a small amino acid.

59. The method according to claim 7, wherein $A^{17}$ is a polar amino acid.

60. The method according to claim 1 wherein $A^{17}$ is missing.

61. The method according to claim 1 wherein $A^{18}$ is OH.

62. The method according to claim 1 wherein $A^{18}$ is $NH_2$.

63. The method according to claim 1 wherein $A^2$–$A^3$ represents 5-aminopentanoic acid, N-Me-antranilic acid, 4-aminocyclohexanecarboxylic acid or 3-aminomethylbenzoic acid.

64. The method according to claim 1 wherein $A^3$–$A^4$ represents N-Me-antranilic acid.

65. The method according to claim 1 wherein n+m is 0–12.

66. The method according to claim 1 wherein at least two residues selected from the group consisting of $A^2$, $A^3$, $A^5$, $A^6$, $A^7$, $A^9$, $A^{10}$, $A^{11}$, $A^{12}$, $A^{13}$, and $A^{16}$ are cyclisation amino acids.

67. The method according to claim 66 wherein two or four of said cyclisation amino acids form one or two bridges selected from disulphide, lactame and Gly-lactame bridges.

68. The method according to claim 67 wherein a disulphide bridge in the compound of formula I are formed between position $A^i$ and $A^{i+3}$ wherein i is an integer selected from 1–14, or between position $A^j$ and $A^{j+6}$ wherein j is an integer selected from 1–11.

69. The method according to claim 67 wherein a lactame bridge in the compound of formula I are formed (i between position $A^k$ and $A^{k+3}$ wherein k is an integer selected from 1–14, or (ii) between position $A^l$ and $A^{l+7}$ wherein l is an integer selected from 1–10, or (iii) between position $A^p$ and $A^{p+6}$ wherein p is an integer selected from 1–11.

70. The method according to claim 67 wherein a Gly-lactame bridge in the compound of formula I is formed between position $A^q$ and $A^{q+4}$ wherein q is an integer selected from 1–13.

71. The method according to claim 1, wherein said compound is selected from the group consisting of A-G-G-F-T-G-A-R-K-S-A-R-K-L-A-N-Q-NH$_2$
F-A-G-F-T-G-A-R-K-S-A-R-K-L-A-N-Q-NH$_2$
F-G-A-F-T-G-A-R-K-S-A-R-K-L-A-N-Q-NH$_2$
F-G-G-A-T-G-A-R-K-S-A-R-K-L-A-N-Q-NH$_2$
F-G-G-F-A-G-A-R-K-S-A-R-K-L-A-N-Q-NH$_2$
F-G-G-F-T-A-A-R-K-S-A-R-K-L-A-N-Q-NH$_2$
F-G-G-F-T-G-A-A-K-S-A-R-K-L-A-N-Q-NH$_2$
F-G-G-F-T-G-A-R-A-S-A-R-K-L-A-N-Q-NH$_2$
F-G-G-F-T-G-A-R-K-A-A-R-K-L-A-N-Q-NH$_2$
F-G-G-F-T-G-A-R-K-S-A-A-K-L-A-N-Q-NH$_2$
F-G-G-F-T-G-A-R-K-S-A-R-A-L-A-N-Q-NH$_2$
F-G-G-F-T-G-A-R-K-S-A-R-K-A-A-N-Q-NH$_2$
F-G-G-F-T-G-A-R-K-S-A-R-K-L-A-A-Q-NH$_2$
F-G-G-F-T-G-A-R-K-S-A-R-K-L-A-A-A-NH$_2$
F-G-G-F-T-G-A-R-K-S-A-A-A-L-A-N-Q-NH$_2$
G-G-F-T-G-A-R-K-S-A-R-K-L-A-N-Q-OH
Ac-F-G-G-F-T-G-A-R-K-S-A-R-K-L-A-N-Q-OH
Ac-G-G-F-T-G-A-R-K-S-A-R-K-L-A-N-Q-OH
(N-Me-Phe)-G-G-F-T-G-A-R-K-S-A-R-K-L-A-N-Q-OH
(Phg)-G-G-F-T-G-A-R-K-S-A-R-K-L-A-N-Q-OH
(hPhe)-G-G-F-T-G-A-R-K-S-A-R-K-L-A-N-Q-OH
Phenylpropionyl-G-G-F-T-G-A-R-K-S-A-R-K-L-A-N-Q-OH
(2Nal)-G-G-F-T-G-A-R-K-S-A-R-K-L-A-N-Q-OH
(N-Bzl-Gly)-G-G-F-T-G-A-R-K-S-A-R-K-L-A-N-Q-OH
(Tic)-G-G-F-T-G-A-R-K-S-A-R-K-L-A-N-Q-OH
(3-Amb)-G-G-F-T-G-A-R-K-S-A-R-K-L-A-N-Q-OH
L-G-G-F-T-G-A-R-K-S-A-R-K-L-A-N-Q-OH
F-(Sar)-T-G-A-R-K-S-A-R-K-L-A-N-Q-NH$_2$
F-a-G-F-T-G-A-R-K-S-A-R-K-L-A-N-Q-NH$_2$
F-(5-Apent)-A-R-K-S-A-R-K-L-A-N-Q-NH$_2$
F-(N-Me anthranilic acid)-F-T-G-A-R-K-S-A-R-K-L-A-N-Q-NH$_2$
F-(4-Aminocyclohexane-carboxylic acid)-F-T-G-A-R-K-S-A-R-K-L-A-N-Q-NH$_2$
F-(3-Amb)-F-T-G-A-R-K-S-A-R-K-L-A-N-Q-NH$_2$
F-p-G-F-T-G-A-R-K-S-A-R-K-L-A-N-Q-NH$_2$
F-G-(Sar)-F-T-G-A-R-K-S-A-R-K-L-A-N-Q-NH$_2$
F-G-(Aib)-F-T-G-A-R-K-S-A-R-K-L-A-N-Q-NH$_2$
F-G-G-(N-Me-Phe)-T-G-A-R-K-S-A-R-K-L-A-N-Q-NH$_2$
F-G-G-(Tic)-T-G-A-R-K-S-A-R-K-L-A-N-Q-OH
F-G-(N-Me anthranilic acid)-T-G-A-R-K-S-A-R-K-L-A-N-Q-NH$_2$
F-G-G-F-(Abu)-G-A-R-K-S-A-R-K-L-A-N-Q-NH$_2$
F-G-G-F-(Val)-G-A-R-K-S-A-R-K-L-A-N-Q-OH
F-G-G-F-T-P-A-R-K-S-A-R-K-L-A-N-Q-NH$_2$
F-G-G-F-T-G-A-K-K-S-A-R-K-L-A-N-Q-NH$_2$
F-G-G-F-T-G-A-H-K-S-A-R-K-L-A-N-Q-NH$_2$
F-G-G-F-T-G-A-Cit-K-S-A-R-K-L-A-N-Q-NH$_2$
F-G-G-F-T-G-A-R-K-S-A-R-K-Y-A-N-Q-NH$_2$
F-G-G-F-R-G-A-T-K-S-A-R-K-L-A-N-Q-NH$_2$
F-G-G-F-r-G-A-T-K-S-A-R-K-L-A-N-Q-NH$_2$
F-G-G-F-T-r-A-A-K-S-A-R-K-L-A-N-Q-NH$_2$
A-(D-2Nal)-G-F-T-G-A-R-K-S-A-R-K-L-A-N-Q-NH$_2$
F-a-G-F-T-A-(Aib)-R-S-L-(Aib)-S-E-F-(Aib)-K-H-NH$_2$
F-c-G-F-c-G-A-R-K-S-A-R-K-L-A-N-Q-NH$_2$
F-C-G-F-C-G-A-R-K-S-A-R-K-L-A-N-Q-NH$_2$
F-c-G-F-C-G-A-R-K-S-A-R-K-L-A-N-Q-NH$_2$
F-c-G-F-(Pen)-G-A-R-K-S-A-R-K-L-A-N-Q-NH$_2$
F-(D-Pen)-G-F-C-G-A-R-K-S-A-R-K-L-A-N-Q-NH$_2$
F-(D-Pen)-G-F-(Pen)-G-A-R-K-S-A-R-K-L-A-N-Q-NH$_2$
F-C-G-F-c-G-A-R-K-S-A-R-K-L-A-N-Q-NH$_2$
F-G-C-F-T-C-A-R-K-S-A-R-K-L-A-N-Q-NH$_2$
F-G-C-F-T-c-A-R-K-S-A-R-K-L-A-N-Q-NH$_2$
F-G-c-F-T-C-A-R-K-S-A-R-K-L-A-N-Q-NH$_2$
F-G-c-F-T-c-A-R-K-S-A-R-K-L-A-N-Q-NH$_2$
F-G-G-F-C-G-A-R-K-S-C-R-K-L-A-N-Q-NH$_2$
F-G-G-F-C-G-A-R-K-S-c-R-K-L-A-N-Q-NH$_2$
F-G-G-F-c-G-A-R-K-S-C-R-K-L-A-N-Q-NH$_2$
F-G-G-F-c-G-A-R-K-S-c-R-K-L-A-N-Q-NH$_2$
F-G-G-F-T-G-c-R-K-C-A-R-K-L-A-N-Q-NH$_2$ -continued F-(D-Asp)-G-F-(Dap)-G-A-R-K-S-A-R-K-L-A-N-Q-NH$_2$
F-(D-Asp)-G-F-T-K-A-R-K-S-A-R-K-L-A-N-Q-NH$_2$
F-G-(Asp)-F-T-G-K-R-K-S-A-R-K-L-A-N-Q-NH$_2$
F-G-(D-Asp)-F-T-G-K-R-K-S-A-R-K-L-A-N-Q-NH$_2$
F-G-(D-Asp)-F-T-G-A-R-(Dap)-S-A-R-K-L-A-N-Q-NH$_2$ (Gly)
F-G-G-F-T-D-A-R-K-(Orn)-A-R-K-L-A-N-Q-NH$_2$ (Gly)
F-G-G-F-T-D-A-R-K-(Orn)-A-NH$_2$ (Gly)
F-G-G-F-T-G-D-R-K-S-Orn-R-K-L-A-N-Q-NH$_2$ and (Gly)
F-c-G-F-C-D-A-R-K-Orn-A-R-K-L-A-N-Q-NH$_2$ 72. The method according to claim 1, wherein the effective amount of the compound is in the range of from about 0.05 to about 100 mg per day, preferably from about 0.1 to about 50 mg per day.

* * * * *

SEQUENCE LISTING

<160> NUMBER OF SEQ ID NOS: 76

<210> SEQ ID NO 1
<211> LENGTH: 17
<212> TYPE: PRT
<213> ORGANISM: Human

<400> SEQUENCE: 1

Ala Gly Gly Phe Thr Gly Ala Arg Lys Ser Ala Arg Lys Leu Ala Asn
1               5                   10                  15
Gln

<210> SEQ ID NO 2
<211> LENGTH: 17
<212> TYPE: PRT
<213> ORGANISM: Human

<400> SEQUENCE: 2

Phe Ala Gly Phe Thr Gly Ala Arg Lys Ser Ala Arg Lys Leu Ala Asn
1               5                   10                  15
Gln

```
<210> SEQ ID NO 3
<211> LENGTH: 17
<212> TYPE: PRT
<213> ORGANISM: Human

<400> SEQUENCE: 3

Phe Gly Ala Phe Thr Gly Ala Arg Lys Ser Ala Arg Lys Leu Ala Asn
 1               5                  10                  15
Gln

<210> SEQ ID NO 4
<211> LENGTH: 17
<212> TYPE: PRT
<213> ORGANISM: Human

<400> SEQUENCE: 4

Phe Gly Gly Ala Thr Gly Ala Arg Lys Ser Ala Arg Lys Leu Ala Asn
 1               5                  10                  15
Gln

<210> SEQ ID NO 5
<211> LENGTH: 17
<212> TYPE: PRT
<213> ORGANISM: Human

<400> SEQUENCE: 5

Phe Gly Gly Phe Ala Gly Ala Arg Lys Ser Ala Arg Lys Leu Ala Asn
 1               5                  10                  15
Gln

<210> SEQ ID NO 6
<211> LENGTH: 17
<212> TYPE: PRT
<213> ORGANISM: Human

<400> SEQUENCE: 6

Phe Gly Gly Phe Thr Ala Ala Arg Lys Ser Ala Arg Lys Leu Ala Asn
 1               5                  10                  15
Gln

<210> SEQ ID NO 7
<211> LENGTH: 17
<212> TYPE: PRT
<213> ORGANISM: Human

<400> SEQUENCE: 7

Phe Gly Gly Phe Thr Gly Ala Ala Lys Ser Ala Arg Lys Leu Ala Asn
 1               5                  10                  15
Gln

<210> SEQ ID NO 8
<211> LENGTH: 17
<212> TYPE: PRT
<213> ORGANISM: Human

<400> SEQUENCE: 8

Phe Gly Gly Phe Thr Gly Ala Arg Ala Ser Ala Arg Lys Leu Ala Asn
 1               5                  10                  15
Gln

<210> SEQ ID NO 9
<211> LENGTH: 17
```

-continued

<212> TYPE: PRT
<213> ORGANISM: Human

<400> SEQUENCE: 9

Phe Gly Gly Phe Thr Gly Ala Arg Lys Ala Ala Arg Lys Leu Ala Asn
 1               5                  10                  15

Gln

<210> SEQ ID NO 10
<211> LENGTH: 17
<212> TYPE: PRT
<213> ORGANISM: Human

<400> SEQUENCE: 10

Phe Gly Gly Phe Thr Gly Ala Arg Lys Ser Ala Ala Lys Leu Ala Asn
 1               5                  10                  15

Gln

<210> SEQ ID NO 11
<211> LENGTH: 17
<212> TYPE: PRT
<213> ORGANISM: Human

<400> SEQUENCE: 11

Phe Gly Gly Phe Thr Gly Ala Arg Lys Ser Ala Arg Ala Leu Ala Asn
 1               5                  10                  15

Gln

<210> SEQ ID NO 12
<211> LENGTH: 17
<212> TYPE: PRT
<213> ORGANISM: Human

<400> SEQUENCE: 12

Phe Gly Gly Phe Thr Gly Ala Arg Lys Ser Ala Arg Lys Ala Ala Asn
 1               5                  10                  15

Gln

<210> SEQ ID NO 13
<211> LENGTH: 17
<212> TYPE: PRT
<213> ORGANISM: Human

<400> SEQUENCE: 13

Phe Gly Gly Phe Thr Gly Ala Arg Lys Ser Ala Arg Lys Leu Ala Ala
 1               5                  10                  15

Gln

<210> SEQ ID NO 14
<211> LENGTH: 17
<212> TYPE: PRT
<213> ORGANISM: Human

<400> SEQUENCE: 14

Phe Gly Gly Phe Thr Gly Ala Arg Lys Ser Ala Arg Lys Leu Ala Ala
 1               5                  10                  15

Ala

<210> SEQ ID NO 15
<211> LENGTH: 17
<212> TYPE: PRT
<213> ORGANISM: Human

<400> SEQUENCE: 15

Phe Gly Gly Phe Thr Gly Ala Arg Lys Ser Ala Ala Ala Leu Ala Asn
 1               5                  10                  15
Gln

<210> SEQ ID NO 16
<211> LENGTH: 16
<212> TYPE: PRT
<213> ORGANISM: Human

<400> SEQUENCE: 16

Gly Gly Phe Thr Gly Ala Arg Lys Ser Ala Arg Lys Leu Ala Asn Gln
 1               5                  10                  15

<210> SEQ ID NO 17
<211> LENGTH: 16
<212> TYPE: PRT
<213> ORGANISM: Human

<400> SEQUENCE: 17

Phe Gly Gly Phe Thr Gly Ala Arg Lys Ser Ala Arg Lys Leu Ala Asn
 1               5                  10                  15

<210> SEQ ID NO 18
<211> LENGTH: 16
<212> TYPE: PRT
<213> ORGANISM: Human

<400> SEQUENCE: 18

Gly Gly Phe Thr Gly Ala Arg Lys Ser Ala Arg Lys Leu Ala Asn Gln
 1               5                  10                  15

<210> SEQ ID NO 19
<211> LENGTH: 17
<212> TYPE: PRT
<213> ORGANISM: Human
<220> FEATURE:
<223> OTHER INFORMATION: Xaa at position 1 is N-Me-Phe

<400> SEQUENCE: 19

Xaa Gly Gly Phe Thr Gly Ala Arg Lys Ser Ala Arg Lys Leu Ala Asn
 1               5                  10                  15
Gln

<210> SEQ ID NO 20
<211> LENGTH: 17
<212> TYPE: PRT
<213> ORGANISM: Human
<220> FEATURE:
<223> OTHER INFORMATION: Xaa at position 1 is Phg

<400> SEQUENCE: 20

Xaa Gly Gly Phe Thr Gly Ala Arg Lys Ser Ala Arg Lys Leu Ala Asn
 1               5                  10                  15
Gln

<210> SEQ ID NO 21
<211> LENGTH: 17
<212> TYPE: PRT
<213> ORGANISM: Human
<220> FEATURE:
<223> OTHER INFORMATION: Xaa at position 1 is hPhe

<400> SEQUENCE: 21

Xaa Gly Gly Phe Thr Gly Ala Arg Lys Ser Ala Arg Lys Leu Ala Asn
1               5                   10                  15

Gln

<210> SEQ ID NO 22
<211> LENGTH: 17
<212> TYPE: PRT
<213> ORGANISM: Human
<220> FEATURE:
<223> OTHER INFORMATION: Xaa at position 1 is Phenylpropionyl

<400> SEQUENCE: 22

Xaa Gly Gly Phe Thr Gly Ala Arg Lys Ser Ala Arg Lys Leu Ala Asn
1               5                   10                  15

Gln

<210> SEQ ID NO 23
<211> LENGTH: 17
<212> TYPE: PRT
<213> ORGANISM: Human
<220> FEATURE:
<223> OTHER INFORMATION: Xaa at position 1 is 2Nal

<400> SEQUENCE: 23

Xaa Gly Gly Phe Thr Gly Ala Arg Lys Ser Ala Arg Lys Leu Ala Asn
1               5                   10                  15

Gln

<210> SEQ ID NO 24
<211> LENGTH: 17
<212> TYPE: PRT
<213> ORGANISM: Human
<220> FEATURE:
<223> OTHER INFORMATION: Xaa at position 1 is N-Bzl-Gly

<400> SEQUENCE: 24

Xaa Gly Gly Phe Thr Gly Ala Arg Lys Ser Ala Arg Lys Leu Ala Asn
1               5                   10                  15

Gln

<210> SEQ ID NO 25
<211> LENGTH: 17
<212> TYPE: PRT
<213> ORGANISM: Human
<220> FEATURE:
<223> OTHER INFORMATION: Xaa at position 1 is Tic

<400> SEQUENCE: 25

Xaa Gly Gly Phe Thr Gly Ala Arg Lys Ser Ala Arg Lys Leu Ala Asn
1               5                   10                  15

Gln

<210> SEQ ID NO 26
<211> LENGTH: 17
<212> TYPE: PRT
<213> ORGANISM: Human
<220> FEATURE:
<223> OTHER INFORMATION: Xaa at position 1 is 3-Amb

<400> SEQUENCE: 26

Xaa Gly Gly Phe Thr Gly Ala Arg Lys Ser Ala Arg Lys Leu Ala Asn
1               5                   10                  15

Gln

<210> SEQ ID NO 27
<211> LENGTH: 17
<212> TYPE: PRT
<213> ORGANISM: Human

<400> SEQUENCE: 27

Leu Gly Gly Phe Thr Gly Ala Arg Lys Ser Ala Arg Lys Leu Ala Asn
 1               5                  10                  15

Gln

<210> SEQ ID NO 28
<211> LENGTH: 15
<212> TYPE: PRT
<213> ORGANISM: Human
<220> FEATURE:
<223> OTHER INFORMATION: Xaa at position 2 is Sar

<400> SEQUENCE: 28

Phe Xaa Thr Gly Ala Arg Lys Ser Ala Arg Lys Leu Ala Asn Gln
 1               5                  10                  15

<210> SEQ ID NO 29
<211> LENGTH: 17
<212> TYPE: PRT
<213> ORGANISM: Human

<400> SEQUENCE: 29

Phe Ala Gly Phe Thr Gly Ala Arg Lys Ser Ala Arg Lys Leu Ala Asn
 1               5                  10                  15

Gln

<210> SEQ ID NO 30
<211> LENGTH: 13
<212> TYPE: PRT
<213> ORGANISM: Human
<220> FEATURE:
<223> OTHER INFORMATION: Xaa at position 2 is 5-Apent

<400> SEQUENCE: 30

Phe Xaa Ala Arg Lys Ser Ala Arg Lys Leu Ala Asn Gln
 1               5                  10

<210> SEQ ID NO 31
<211> LENGTH: 16
<212> TYPE: PRT
<213> ORGANISM: Human
<220> FEATURE:
<223> OTHER INFORMATION: Xaa at position 2 is N-Me anthranilic acid

<400> SEQUENCE: 31

Phe Xaa Phe Thr Gly Ala Arg Lys Ser Ala Arg Lys Leu Ala Asn Gln
 1               5                  10                  15

<210> SEQ ID NO 32
<211> LENGTH: 16
<212> TYPE: PRT
<213> ORGANISM: Human
<220> FEATURE:
<223> OTHER INFORMATION: Xaa at position 2 is 4-Aminocyclohexane-
        carboxylic acid

<400> SEQUENCE: 32

Phe Xaa Phe Thr Gly Ala Arg Lys Ser Ala Arg Lys Leu Ala Asn Gln
 1               5                  10                  15

-continued

```
<210> SEQ ID NO 33
<211> LENGTH: 16
<212> TYPE: PRT
<213> ORGANISM: Human
<220> FEATURE:
<223> OTHER INFORMATION: Xaa at position 2 is 3-Amb

<400> SEQUENCE: 33

Phe Xaa Phe Thr Gly Ala Arg Lys Ser Ala Arg Lys Leu Ala Asn Gln
 1               5                  10                  15

<210> SEQ ID NO 34
<211> LENGTH: 17
<212> TYPE: PRT
<213> ORGANISM: Human

<400> SEQUENCE: 34

Phe Pro Gly Phe Thr Gly Ala Arg Lys Ser Ala Arg Lys Leu Ala Asn
 1               5                  10                  15

Gln

<210> SEQ ID NO 35
<211> LENGTH: 17
<212> TYPE: PRT
<213> ORGANISM: Human
<220> FEATURE:
<223> OTHER INFORMATION: Xaa at position 3 is Sar

<400> SEQUENCE: 35

Phe Gly Xaa Phe Thr Gly Ala Arg Lys Ser Ala Arg Lys Leu Ala Asn
 1               5                  10                  15

Gln

<210> SEQ ID NO 36
<211> LENGTH: 17
<212> TYPE: PRT
<213> ORGANISM: Human
<220> FEATURE:
<223> OTHER INFORMATION: Xaa at position 3 is Aib

<400> SEQUENCE: 36

Phe Gly Xaa Phe Thr Gly Ala Arg Lys Ser Ala Arg Lys Leu Ala Asn
 1               5                  10                  15

Gln

<210> SEQ ID NO 37
<211> LENGTH: 17
<212> TYPE: PRT
<213> ORGANISM: Human
<220> FEATURE:
<223> OTHER INFORMATION: Xaa at position 4 is N-Me-Phe

<400> SEQUENCE: 37

Phe Gly Gly Xaa Thr Gly Ala Arg Lys Ser Ala Arg Lys Leu Ala Asn
 1               5                  10                  15

Gln

<210> SEQ ID NO 38
<211> LENGTH: 17
<212> TYPE: PRT
<213> ORGANISM: Human
<220> FEATURE:
<223> OTHER INFORMATION: Xaa at position 4 is Tic

<400> SEQUENCE: 38
```

```
Phe Gly Gly Xaa Thr Gly Ala Arg Lys Ser Ala Arg Lys Leu Ala Asn
1               5                   10                  15

Gln

<210> SEQ ID NO 39
<211> LENGTH: 16
<212> TYPE: PRT
<213> ORGANISM: Human
<220> FEATURE:
<223> OTHER INFORMATION: Xaa at position 3 is N-Me anthranilic acid

<400> SEQUENCE: 39

Phe Gly Xaa Thr Gly Ala Arg Lys Ser Ala Arg Lys Leu Ala Asn Gln
1               5                   10                  15

<210> SEQ ID NO 40
<211> LENGTH: 17
<212> TYPE: PRT
<213> ORGANISM: Human
<220> FEATURE:
<223> OTHER INFORMATION: Xaa at position 5 is Abu

<400> SEQUENCE: 40

Phe Gly Gly Phe Xaa Gly Ala Arg Lys Ser Ala Arg Lys Leu Ala Asn
1               5                   10                  15

Gln

<210> SEQ ID NO 41
<211> LENGTH: 17
<212> TYPE: PRT
<213> ORGANISM: Human
<220> FEATURE:
<223> OTHER INFORMATION: Xaa at position 5 is Val

<400> SEQUENCE: 41

Phe Gly Gly Phe Xaa Gly Ala Arg Lys Ser Ala Arg Lys Leu Ala Asn
1               5                   10                  15

Gln

<210> SEQ ID NO 42
<211> LENGTH: 17
<212> TYPE: PRT
<213> ORGANISM: Human

<400> SEQUENCE: 42

Phe Gly Gly Phe Thr Pro Ala Arg Lys Ser Ala Arg Lys Leu Ala Asn
1               5                   10                  15

Gln

<210> SEQ ID NO 43
<211> LENGTH: 17
<212> TYPE: PRT
<213> ORGANISM: Human

<400> SEQUENCE: 43

Phe Gly Gly Phe Thr Gly Ala Lys Lys Ser Ala Arg Lys Leu Ala Asn
1               5                   10                  15

Gln

<210> SEQ ID NO 44
<211> LENGTH: 17
<212> TYPE: PRT
<213> ORGANISM: Human
```

<400> SEQUENCE: 44

Phe Gly Gly Phe Thr Gly Ala His Lys Ser Ala Arg Lys Leu Ala Asn
 1               5                  10                  15

Gln

<210> SEQ ID NO 45
<211> LENGTH: 17
<212> TYPE: PRT
<213> ORGANISM: Human
<220> FEATURE:
<223> OTHER INFORMATION: Xaa at position 8 is Cit

<400> SEQUENCE: 45

Phe Gly Gly Phe Thr Gly Ala Xaa Lys Ser Ala Arg Lys Leu Ala Asn
 1               5                  10                  15

Gln

<210> SEQ ID NO 46
<211> LENGTH: 17
<212> TYPE: PRT
<213> ORGANISM: Human

<400> SEQUENCE: 46

Phe Gly Gly Phe Thr Gly Ala Arg Lys Ser Ala Arg Lys Tyr Ala Asn
 1               5                  10                  15

Gln

<210> SEQ ID NO 47
<211> LENGTH: 17
<212> TYPE: PRT
<213> ORGANISM: Human

<400> SEQUENCE: 47

Phe Gly Gly Phe Arg Gly Ala Thr Lys Ser Ala Arg Lys Leu Ala Asn
 1               5                  10                  15

Gln

<210> SEQ ID NO 48
<211> LENGTH: 17
<212> TYPE: PRT
<213> ORGANISM: Human

<400> SEQUENCE: 48

Phe Gly Gly Phe Arg Gly Ala Thr Lys Ser Ala Arg Lys Leu Ala Asn
 1               5                  10                  15

Gln

<210> SEQ ID NO 49
<211> LENGTH: 17
<212> TYPE: PRT
<213> ORGANISM: Human

<400> SEQUENCE: 49

Phe Gly Gly Phe Thr Arg Ala Ala Lys Ser Ala Arg Lys Leu Ala Asn
 1               5                  10                  15

Gln

<210> SEQ ID NO 50
<211> LENGTH: 17
<212> TYPE: PRT
<213> ORGANISM: Human

-continued

<220> FEATURE:
<223> OTHER INFORMATION: Xaa at position 2 is D-2Nal

<400> SEQUENCE: 50

Ala Xaa Gly Phe Thr Gly Ala Arg Lys Ser Ala Arg Lys Leu Ala Asn
 1               5                  10                  15

Gln

<210> SEQ ID NO 51
<211> LENGTH: 17
<212> TYPE: PRT
<213> ORGANISM: Human
<220> FEATURE:
<223> OTHER INFORMATION: Xaa at positions 7, 11, and 15  is Aib

<400> SEQUENCE: 51

Phe Ala Gly Phe Thr Ala Xaa Arg Ser Leu Xaa Ser Glu Phe Xaa Lys
 1               5                  10                  15

His

<210> SEQ ID NO 52
<211> LENGTH: 17
<212> TYPE: PRT
<213> ORGANISM: Human

<400> SEQUENCE: 52

Phe Cys Gly Phe Cys Gly Ala Arg Lys Ser Ala Arg Lys Leu Ala Asn
 1               5                  10                  15

Gln

<210> SEQ ID NO 53
<211> LENGTH: 17
<212> TYPE: PRT
<213> ORGANISM: Human

<400> SEQUENCE: 53

Phe Cys Gly Phe Cys Gly Ala Arg Lys Ser Ala Arg Lys Leu Ala Asn
 1               5                  10                  15

Gln

<210> SEQ ID NO 54
<211> LENGTH: 17
<212> TYPE: PRT
<213> ORGANISM: Human

<400> SEQUENCE: 54

Phe Cys Gly Phe Cys Gly Ala Arg Lys Ser Ala Arg Lys Leu Ala Asn
 1               5                  10                  15

Gln

<210> SEQ ID NO 55
<211> LENGTH: 17
<212> TYPE: PRT
<213> ORGANISM: Human
<220> FEATURE:
<223> OTHER INFORMATION: Xaa at position 5 is Pen

<400> SEQUENCE: 55

Phe Cys Gly Phe Xaa Gly Ala Arg Lys Ser Ala Arg Lys Leu Ala Asn
 1               5                  10                  15

Gln

<210> SEQ ID NO 56
<211> LENGTH: 17
<212> TYPE: PRT
<213> ORGANISM: Human
<220> FEATURE:
<223> OTHER INFORMATION: Xaa at position 2 is D-Pen

<400> SEQUENCE: 56

Phe Xaa Gly Phe Cys Gly Ala Arg Lys Ser Ala Arg Lys Leu Ala Asn
 1               5                  10                  15

Gln

<210> SEQ ID NO 57
<211> LENGTH: 17
<212> TYPE: PRT
<213> ORGANISM: Human
<220> FEATURE:
<223> OTHER INFORMATION: Xaa at position 2 is D-Pen
      Xaa at position 5 is Pen

<400> SEQUENCE: 57

Phe Xaa Gly Phe Xaa Gly Ala Arg Lys Ser Ala Arg Lys Leu Ala Asn
 1               5                  10                  15

Gln

<210> SEQ ID NO 58
<211> LENGTH: 17
<212> TYPE: PRT
<213> ORGANISM: Human

<400> SEQUENCE: 58

Phe Cys Gly Phe Cys Gly Ala Arg Lys Ser Ala Arg Lys Leu Ala Asn
 1               5                  10                  15

Gln

<210> SEQ ID NO 59
<211> LENGTH: 17
<212> TYPE: PRT
<213> ORGANISM: Human

<400> SEQUENCE: 59

Phe Gly Cys Phe Thr Cys Ala Arg Lys Ser Ala Arg Lys Leu Ala Asn
 1               5                  10                  15

Gln

<210> SEQ ID NO 60
<211> LENGTH: 17
<212> TYPE: PRT
<213> ORGANISM: Human

<400> SEQUENCE: 60

Phe Gly Cys Phe Thr Cys Ala Arg Lys Ser Ala Arg Lys Leu Ala Asn
 1               5                  10                  15

Gln

<210> SEQ ID NO 61
<211> LENGTH: 17
<212> TYPE: PRT
<213> ORGANISM: Human

<400> SEQUENCE: 61

Phe Gly Cys Phe Thr Cys Ala Arg Lys Ser Ala Arg Lys Leu Ala Asn
 1               5                  10                  15

Gln

<210> SEQ ID NO 62
<211> LENGTH: 17
<212> TYPE: PRT
<213> ORGANISM: Human

<400> SEQUENCE: 62

Phe Gly Cys Phe Thr Cys Ala Arg Lys Ser Ala Arg Lys Leu Ala Asn
 1               5                  10                  15

Gln

<210> SEQ ID NO 63
<211> LENGTH: 17
<212> TYPE: PRT
<213> ORGANISM: Human

<400> SEQUENCE: 63

Phe Gly Gly Phe Cys Gly Ala Arg Lys Ser Cys Arg Lys Leu Ala Asn
 1               5                  10                  15

Gln

<210> SEQ ID NO 64
<211> LENGTH: 17
<212> TYPE: PRT
<213> ORGANISM: Human

<400> SEQUENCE: 64

Phe Gly Gly Phe Cys Gly Ala Arg Lys Ser Cys Arg Lys Leu Ala Asn
 1               5                  10                  15

Gln

<210> SEQ ID NO 65
<211> LENGTH: 17
<212> TYPE: PRT
<213> ORGANISM: Human

<400> SEQUENCE: 65

Phe Gly Gly Phe Cys Gly Ala Arg Lys Ser Cys Arg Lys Leu Ala Asn
 1               5                  10                  15

Gln

<210> SEQ ID NO 66
<211> LENGTH: 17
<212> TYPE: PRT
<213> ORGANISM: Human

<400> SEQUENCE: 66

Phe Gly Gly Phe Cys Gly Ala Arg Lys Ser Cys Arg Lys Leu Ala Asn
 1               5                  10                  15

Gln

<210> SEQ ID NO 67
<211> LENGTH: 17
<212> TYPE: PRT
<213> ORGANISM: Human

<400> SEQUENCE: 67

Phe Gly Gly Phe Thr Gly Cys Arg Cys Ala Arg Lys Leu Ala Asn
 1               5                  10                  15

Gln

<210> SEQ ID NO 68
<211> LENGTH: 17
<212> TYPE: PRT
<213> ORGANISM: Human
<220> FEATURE:
<223> OTHER INFORMATION: Xaa at position 2 is D-Asp
      Xaa at position 5 is Dap

<400> SEQUENCE: 68

Phe Xaa Gly Phe Xaa Gly Ala Arg Lys Ser Ala Arg Lys Leu Ala Asn
 1               5                  10                  15

Gln

<210> SEQ ID NO 69
<211> LENGTH: 17
<212> TYPE: PRT
<213> ORGANISM: Human
<220> FEATURE:
<223> OTHER INFORMATION: Xaa at position 2 is D-Asp

<400> SEQUENCE: 69

Phe Xaa Gly Phe Thr Lys Ala Arg Lys Ser Ala Arg Lys Leu Ala Asn
 1               5                  10                  15

Gln

<210> SEQ ID NO 70
<211> LENGTH: 17
<212> TYPE: PRT
<213> ORGANISM: Human
<220> FEATURE:
<223> OTHER INFORMATION: Xaan at position 3 is Asp

<400> SEQUENCE: 70

Phe Gly Xaa Phe Thr Gly Lys Arg Lys Ser Ala Arg Lys Leu Ala Asn
 1               5                  10                  15

Gln

<210> SEQ ID NO 71
<211> LENGTH: 17
<212> TYPE: PRT
<213> ORGANISM: Human
<220> FEATURE:
<223> OTHER INFORMATION: Xaa at position 3 is D-Asp

<400> SEQUENCE: 71

Phe Gly Xaa Phe Thr Gly Lys Arg Lys Ser Ala Arg Lys Leu Ala Asn
 1               5                  10                  15

Gln

<210> SEQ ID NO 72
<211> LENGTH: 16
<212> TYPE: PRT
<213> ORGANISM: Human
<220> FEATURE:
<223> OTHER INFORMATION: Xaa at position 3 is D-Asp

<400> SEQUENCE: 72

Phe Gly Xaa Phe Thr Gly Ala Arg Ser Ala Arg Lys Leu Ala Asn Gln
 1               5                  10                  15

<210> SEQ ID NO 73
<211> LENGTH: 17
<212> TYPE: PRT
<213> ORGANISM: Human

```
<220> FEATURE:
<223> OTHER INFORMATION: Xaa at position 10 is Orn

<400> SEQUENCE: 73

Phe Gly Gly Phe Thr Asp Ala Arg Lys Xaa Ala Arg Lys Leu Ala Asn
1               5                   10                  15

Gln

<210> SEQ ID NO 74
<211> LENGTH: 11
<212> TYPE: PRT
<213> ORGANISM: Human
<220> FEATURE:
<223> OTHER INFORMATION: Xaa at position 10 is Orn

<400> SEQUENCE: 74

Phe Gly Gly Phe Thr Asp Ala Arg Lys Xaa Ala
1               5                   10

<210> SEQ ID NO 75
<211> LENGTH: 17
<212> TYPE: PRT
<213> ORGANISM: Human
<220> FEATURE:
<223> OTHER INFORMATION: Xaa at position 11 is Orn

<400> SEQUENCE: 75

Phe Gly Gly Phe Thr Gly Asp Arg Lys Ser Xaa Arg Lys Leu Ala Asn
1               5                   10                  15

Gln

<210> SEQ ID NO 76
<211> LENGTH: 17
<212> TYPE: PRT
<213> ORGANISM: Human
<220> FEATURE:
<223> OTHER INFORMATION: Xaa at position 10 is Orn

<400> SEQUENCE: 76

Phe Cys Gly Phe Cys Asp Ala Arg Lys Xaa Ala Arg Lys Leu Ala Asn
1               5                   10                  15

Gln
```